United States Patent
Pankewycz

(10) Patent No.: US 7,253,148 B2
(45) Date of Patent: Aug. 7, 2007

(54) HUMAN GENE WITH IMMUNOREGULATORY AND ANTI-PROLIFERATIVE PROPERTIES

(75) Inventor: Oleh G. Pankewycz, Amherst, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 10/972,233

(22) Filed: Oct. 22, 2004

(65) Prior Publication Data

US 2005/0282178 A1    Dec. 22, 2005

Related U.S. Application Data

(63) Continuation-in-part of application No. 10/795,766, filed on Mar. 8, 2004, now abandoned.

(60) Provisional application No. 60/452,780, filed on Mar. 7, 2003.

(51) Int. Cl.
*A61K 38/00*   (2006.01)

(52) U.S. Cl. ..................................... 514/12

(58) Field of Classification Search ............... 530/350; 536/23.1; 435/69.1
See application file for complete search history.

(56) References Cited

U.S. PATENT DOCUMENTS

2003/0186360 A1   10/2003   Feder et al.

FOREIGN PATENT DOCUMENTS

WO    WO 01/89555 A1    11/2001
WO    WO 03/016476 A2    2/2003

OTHER PUBLICATIONS

GenCore version 5.1.6, pp. 1-2, relevant to SEQ ID No. 1.*
Barneoud et al., Quantitative motor assessement in FALS mice: a longitudinal study, NeuroReport vol. 8, p. 2861-2865 (1997).
Sequence search results (10) provided with International Search Report.

* cited by examiner

*Primary Examiner*—Karen Cochrane Carlson
*Assistant Examiner*—Agnes B. Rooke
(74) *Attorney, Agent, or Firm*—Hodgson Russ LLP

(57) ABSTRACT

This invention describes the human gene homologue of the mouse gene previously identified. The human gene is located on the long arm of chromosome 17. The human gene, termed G1h, encodes for a protein, termed P1h, that substantially differs from the mouse protein. The human protein P1h can be used for immunosuppressive actions and clinical applications.

13 Claims, 19 Drawing Sheets

Figure 1

```
AAAAAGGATA ACTTTAACCG AAGGAAGGGT TTGGTTCCAT TCAACTCCAC ATTCATTGTG
CCTTTACTTG CATTAGATTT CTGTGCTTTC TTCCTTTCCC TCTTTGAAGC AATTAAAATC
TTCCTTGATA ACTGCTGTTT CTTTCTACTC TTGTTTCTGG CAATTTAGTG GGTTCCTTCT
CTAGTGGTCT TAAATCTCAT TCCACTGGTG GCAAGATGGG GCCTAGCCTT CTTTTCACAT
GTCTAATCTT TTCCTTTCTC ATGGTGCCCT CCATGGAAGT CACAGTCAAC ACTGAATAAA
TGACTAGAAT GACACGTGTG CGTGCGCACG CGTGTGCGTG TGTGTGTTCA TCTGTCTGCA
TGTCCATCAA TTTCTTTTAG AAAATAATTT ATTGTATGAT TTATTTGGA GTTATATTCT
GATTACAGTG CTCCCTCTCC CAAATAGCAT TGATTTTTTC CCCCCTCTAA AATGTATAAT
CTGGTCTCAG GTTGGATTCT TTGGTACATT TCTCTCTTCT GGATGCCATG CAGCTTAATT
AAAACCTTGC TTAAAAACAA AAAGTGAAAA TTGTGTACTC TTGTCTGGAA TACCGCCTCA
```

Figure 2

HumanG1h TGACTAGAAT GACACGTGTG CGTGCGCACG CGTGTGCGTG TGTGTGTTCA
TCTGTCTGCA

MouseG1   AACACTGAGT AAGAGACCAG AGTGATTGTG TGCATGTGCG CGTGTGTGTG
TCCATCTGCA

HumanG1h TGTCCATCAA TTTCTTTTAG AAAA-TAATTT ATTGTATGAT TTATTTTGGA
GTTATATTCT

MouseG1   TGTGCGTCAG TTTCTTT--G AAAAATAATTT ATTGTGTGAT TTCCTGTGGA
GTTTTTGTTC

HumanG1h GATTACAGTG CTCCCTCTCC CAAATAGCAT TGATTTTTTC CCCCCTCTAA
AATGTATAAT

MouseG1   AGGTTACAGT GCTGCTCCAC A--ATAGCAC GGATCCCTGT CCCCCTACCC
CCGGCATAAA

HumanG1h CTGGTCTCAG GTTGGATTCT TTGGTACATT TCTCTCTTCT GGATGCCATG
CAGCTTAATT

MouseG1   ATGTATTATC TGGTCTCAGG TTGGATTCCT TGGTACAGTT TCTTTCTGTG
CAGTTTATTA

Figure 3A

Human P1h Sequence: MTRIDTCAC ARVCVCVFI CLHVDQFLL ENNLLYDLFW

Mouse P1 Sequence:  M- - - - - CA - - - - CVC - - - C - - V - - - - L – NNLL- D - -W Human P1h Sequence: SYILITVLPL PNSIDFFPP LKCIIWSQVG FFGTFLSSGC HAA Mouse P1 Sequence:  S - - - TVL- L - NS-D- - PP

Figure 3B

Human P1h Sequence: MTRIDTCAC ARVCVCVFI CLHVDQFLL ENNLLYDLFW

Mouse P1 Sequence:  M- - - - - CA - - - - CVC - - - C - - V - - - - L – NNLL- D - -W Human P1h Sequence: SYILITVLPL PNSIDFFPP LKCIIWSQVG FFGTFLSSGC HAA Mouse P1 Sequence:  S - - - TVL- L - NS-D- - PP – KCIIWSQVG F- GT- - - - - - - - - - - - - - -

Figure 17B

P1H is inserted into pYES2NT-B in right frame

5'G GGT TCT CAT CAT CAT CAT CAT CAT GGT ATG GCT AGC ATG
ACT GGT GGA CAG CAA ATG GGT CGG GAT CTG TAC GAC GAT GAC
GAT AAG GTA CCT AAG GAT CCA GTG TGG TGG AAT TCG CCC TTG
[ATG]CTAGAATCGACACGTGTGCGTGCGCACGCGTGTGCGTGTGTGTTCA
TCTGTCTGCATGTGGATCAATTTCTTTTAGAAAATAATTTATTGTATGATTTAT
TTTGGAGTTATATTCTGATTACAGTGCTCCCTCTCCCAAATAGCATTGATTTTT
TCCCCCCTCTAAAATGTATAATCTGGTCTCAGGTTGGATTCTTTGGTACATTT
CTCTCTTCTGGATGCCATGCAGCT[TAA]GAA GGG CGA ATT CTG CAG ATA
TCC AGC ACA GTG GCG GCC GCT CGA GTC TAG AGG GCC CTT CGA AGG
TAAGCCTATCCCTAACCCTCTCCTCGGTCTCGATTCTACGCGTACCGGTCATC
ATCACCATCACCATTGAGTTTAAACCCGCTGATCCTAGAGGGCCGCATCATGT
AATTAGTTATGTCACGCTTACATTCACGCCCTCCCCCCACATCCGCTCTAACC
GAAAAGGAAGGAGTTAGACAACCTGAAGTCTAGGTCCCTATTTATTTTTTTAT
AGTTATGTTAGTATTAAGAACGTTATTTATATTTCAAATTTTTCTTTTTTTTCT
GTACAGACGCGTGTACGCATGTAACATTATACTGAAAACCTTGCTTGAGAAG
GTTTTGGGACGCTCGAAGGCTTTAATTTGCAAGCTGCGGCCCTGCATTAATG
AATCGGCCAACGCGCGGGGAGAGGCGGTTTGCGTATTGGGCGCTCTTCCGCT
TCCTCGCTCACTGACTCGCTGC3'

HUMAN GENE WITH IMMUNOREGULATORY AND ANTI-PROLIFERATIVE PROPERTIES

This application is a continuation in part of U.S. Non-provisional application Ser. No. 10/795,766 filed on Mar. 8, 2004, now abandoned which in turn claims priority to U.S. provisional application Ser. No. 60/452,780, filed on Mar. 7, 2003, the disclosures of which are incorporated herein by reference.

FIELD OF THE INVENTION

The present invention relates generally to the field of immunoregulation and growth inhibition.

DISCUSSION OF RELATED ART

Many human disorders are caused by disregulated activation of the immune system, including but not limited to type 1 diabetes, multiple sclerosis, systemic lupus erythematosus, autoimmune thyroiditis, ulcerative colitis and regional enteritis. Moreover, many human cancers are associated with a generalized immunosuppressive state. Uncovering the molecules responsible for controlling abnormal immunity or the molecules that are aberrantly produced in cancer cells that suppress the immune state would greatly aid in the therapy of these disorders. Such molecules could be used as therapeutic agents to restore normal immunity during states of autoimmunity. Alternatively, such molecules may be used as targets to generate inhibitory antibodies or small molecules that would restore normal immunity in states of immunodeficiency.

Human Type 1 diabetes mellitus (IDDM) is a disorder caused by an aberrant immune response directed specifically against the insulin producing pancreatic islet beta cells. It is now clear that in patients with IDDM, T lymphocytes recognize self antigens expressed on beta cells such as glutamic acid decarboxylase (GAD), insulin and other proteins as being foreign leading to their destruction. Under normal conditions, such a deviant autoimmune anti-beta cell immune reaction is controlled at several levels. Immune tolerance is usually achieved through "central" or thymic T cell deletion of autoreactive T cells or by peripheral mechanisms designed to silence or "suppress" the reactivity of autoimmune T cells. Several different cell types have been proposed as mediators of peripheral immune suppression including both CD4 and CD8 positive T cells, however, the mechanisms by which these cells modulate an immune response remains enigmatic. By identifying molecules that mediate natural T cell immunosuppression, investigators and physicians may exploit this pathway to treat a variety of autoimmune diseases as well as states of immunodeficiency.

Previously, a CD8 positive T lymphocyte clone (single cell type) that prevents autoimmune diabetes in a mouse model of human IDDM was described (Pankewycz et. al. 1991. Eur. J. Immunology 21: 873-879). In further experiments, this T cell clone, IS 2.15, was demonstrated to secrete a soluble molecule that inhibits the proliferation of lymphocytes in response to a strong immunological stimulus, namely alloantigen (Pankewycz et. al. 1992. Eur. J. Immunol. 22: 2017-2023). Further, a single protein derived from IS 2.15 T cells was demonstrated to reproduce the inhibitory activity of the T cell clone itself. This peptide was identified (WO 01/89555) as MCACVCPSACASVSLKNNLLCDFL-WSFCSGYSAAPQ (SEQ ID NO:4).

SUMMARY OF THE INVENTION

This Present invention describes the identification of a novel human gene (G1h) and its corresponding protein (P1h). This gene is expressed in many tissues but demonstrates selectivity in relation to the proliferative state or the immunostimulatory state. The human gene is located on the long arm of chromosome 17. The human gene, termed G1h, encodes for a protein, termed P1h, that substantially differs from the mouse protein. The human protein, P1h, can be used for immunosuppressive actions and clinical applications for proliferative disorders.

BRIEF DESCRIPTION OF THE DRAWINGS

FIG. 1. Genomic structure of Human G1h. Human G1h (SEQ ID NO:5) is a single exon gene (solid underlining) containing a 5' consensus TATA box (dashed underlining) required for transcription and a typical 3' Poly-A signal (waved underlining) for mRNA transcription. G1h has a STAT-1 binding site (dot-dash underline).

FIG. 2. Genomic similarity between Human G1h and mouse gene G1 (722145) coding regions. Both the human G1h and mouse G1 genes share sequence similarities in the middle portion of the coding region. The human gene with the start site (ATG) underlined in bold and the stop site (TAA) underlined in bold is shown. The mouse G1 sequence homologous region is also shown. The gene identity is depicted in plain underlining. Other than the significant homology within the mid-region of the encoding region, the two genes are generally dissimilar FIGS. 3A and 3B. A comparison of the human P1h peptide and mouse peptide P1 (FIG. 3A) and of human P1h peptide and mouse P1B peptide (FIG. 3B).

In FIG. 8A, G1h expression was measured in various cancer cell lines by PCR. Cancer cells were harvested either in a resting (confluent) state or during the logarithmic phase of growth. In FIG. 8B, the expression of human G1h gene in cancer cell lines was equalized to actin expression. Both the lung and prostate cancer cell lines appeared to overexpress G1h.

FIG. 17B is a representation of the results of direct sequencing of the pYES/NT vector. The sequence of yeast expression vector was confirmed to be "in frame" with appropriate start and stop codons. The sequence of G1h is underlined with start and stop codons in boxes (SEQ ID NO:17).

DETAILED DESCRIPTION OF THE INVENTION

Figure 4:
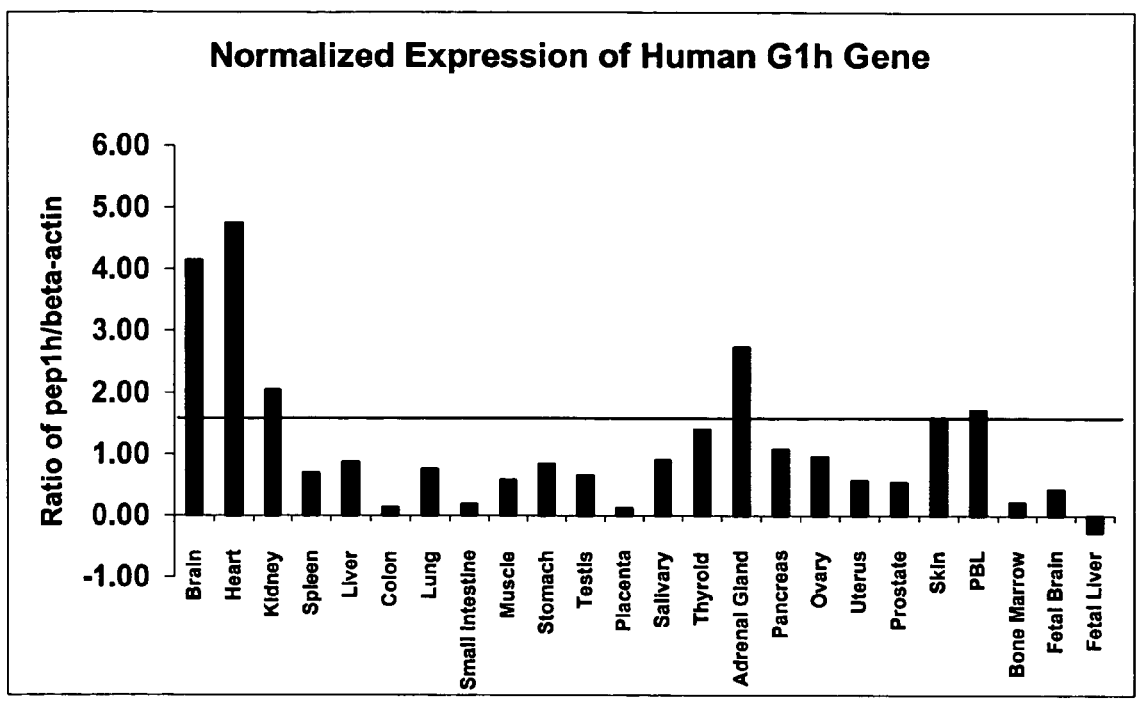
FIG. 4. Gene expression pattern of human G1h. Human G1h expression was examined using PCR techniques. The expression of G1h was compared to that of a common "housekeeping" gene, beta actin for the indicated tissues. A ratio of G1h:actin of greater than one suggests that G1h expression is stimulated in a particular organ. A ratio of zero or a negative ratio suggests that G1h is modestly stimulated or actively downregulated respectively.

This application describes a human gene (G1h) encoding a protein which is regulated during development and T-cell activation. The polynucleotide of the present invention comprises a sequence of SEQ ID NO:1, a degenerate sequence of SEQ ID NO:1 and may also have a sequence which hybridizes to SEQ ID NO:1 under stringent conditions. A portion of the gene encodes for a protein termed herein as the P1h protein.

By "degenerate sequence" is meant a sequence in which a different codon is used to specify the insertion of the same amino acid in a peptide chain. Degenerate sequence codons are well known to those skilled in the art. Further, sequences which result in conservative substitutions of amino acids such that the function of the protein is not affected are also within the scope of this invention.

By "stringent conditions" is meant hybridization under conditions of temperature and salt concentration which result in duplex DNA molecules formed only between strands in which greater than 90% of the nucleotide bases are paired.

The human gene has a similar chromosomal location as the mouse gene. However, the amino acid sequence is significantly different. This gene appears to be regulated during growth and is also regulated during T cell activation. The protein encoded by the G1h gene is 79 amino acids long.

The present invention provides vectors which contain polynucleotides encoding the P1h peptide or biologically fragments or variants thereof. The present invention also provides host cells which are genetically engineered with vectors of the invention. Host cells can be genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in standard nutrient media modified as appropriate for activating promoters, selecting transformants or amplifying the G1h gene.

The polynucleotides of the present invention may be used for producing polypeptides by recombinant techniques. For example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct mRNA synthesis. Suitable promoters are well known those skilled in the art. The vector containing the appropriate DNA sequence and an appropriate promoter or control sequence, can be used to transform a host for expression of the protein.

In one embodiment of the invention are provided isolated nucleic sequences (DNA or RNA) which encode the P1h protein or a biological active fragment of variant thereof. These nucleic acid sequences can be used as PCR primers or as hybridization probes. The nucleic acid molecules may be single stranded or double stranded DNA or RNA and also include sequences complementary to the sequences disclosed herein. By "isolated sequence" is meant that the nucleic acid is purified from the setting in which it is found in nature. By "RNA sequence corresponding to a DNA sequence" is meant that Ts in the DNA are replaced with Us. The hybridization probes may be used to detect identical, similar or complementary nucleic acid sequences. The length and hybridization conditions for using the probes are well within the purview of those skilled in the art.

Nucleic acid probes based on the sequence of G1h and its coding region may be used as part of a diagnostic kit for identifying cells or tissues with altered expression of the G1h gene, such as in obesity, cancer or immune disorders. In addition, these probes may be also used for identifying polymorphisms. To compare the expression of G1h in any diseased state, a sample of a tissue is can be obtained and the expression of G1h determined and compared with a matched normal tissue. A matched normal tissue may be sample from the same individual from a different tissue or from the same tissue in the absence of the diseased state or from another individual who does not have the diseased state.

In another embodiment of the invention is provided a polypeptide sequence designated herein as P1h. Also included within the scope of the present invention are fragments of P1h which have at least one biological activity of the P1h protein. The protein P1h or fragments thereof can be used for diagnostic assays, to generate antibodies that are reactive against the P1h protein or for therapeutic purposes. The generation of antibodies, both monoclonal and polyclonal, is well known to those skilled in the art.

The data presented herein demonstrates that this gene is differentially expressed in various adult tissues but it is undetectable in human fetal tissues. These data suggest that the human gene is involved in fetal development and may be abnormal in disorders of development. The human gene is regulated in vivo in states of active systemic lupus erythematosus (SLE) and obesity further strengthening its biological significance. Furthermore, the levels of G1h in peripheral blood cells decrease during hyperglycemia. These results suggest that the human gene and by inference the human protein is involved in glucose homeostasis and perhaps diabetes. The human gene is also shown to be expressed in human cancers implicating its unique potential significance in oncological disorders. In addition, the human gene G1h is expressed in endothelial cells and is regulated by inflammatory cytokines. These findings suggest that the human gene is linked to disorders of vascular biology such as atherosclerosis, glomerulonephritis and vasculitis. Thus, the human gene appears to be expressed in a variety of cell types, disease states and metabolic derangements suggesting that it is involved in general homeostatic processes not limited to inflammation and autoimmunity.

The protein (P1h) encoded by the novel human gene G1h has growth inhibitory activity. Therefore, the human protein may serve as a therapeutic agent to alleviate or cure autoimmunity. Alternatively, therapies designed to inhibit this gene (anti-sense RNA or DNA) or the protein product (antibodies or small molecules) may improve immune functions. In the present invention, it is also demonstrated that the human G1h gene is present in T lymphocytes, B lymphocytes and macrophages and that the expression of G1h is down regulated upon cellular activation. Moreover, G1h expression was diminished in peripheral blood cells in vivo in a patient with active systemic lupus erythematosus. These findings suggest that the human G1h gene and consequently the P1h protein is involved in multiple pathways of immune functioning and pathogenic immunological diseases. Such unique pathways include (1) the promotion or inhibition of antibody formation (2) the activation of the innate immune system in macrophages. These unique functions may play a role in improving human responses to infections, immunizations and cancers by promoting immunotherapeutic strategies or inhibiting states of immune disregulation.

Accordingly, based on the ability of P1h to inhibit T cell proliferation, compositions comprising P1h or its active fragments can be used for preventing or treating autoimmune disease, transplant rejection, or proliferative disorders. By active fragments or variants thereof is meant shorter or longer sequences of P1h which have substantial similarity with the sequence of SEQ ID NO:2 and also have similar biological activity. The protein, or active fragments or variants thereof can be administered in a pharmaceutically acceptable carrier. Suitable carriers are well know to those skilled in the art and include aqueous solutions of salts or buffers, topical creams of lotions, and solid dosage forms such as pills, gelatin capsules, or liquid-filled gelatin tables. Peptides are also often administered in the form of nontoxic salts such as hydrochloride, hydrobromide, sulfate, phosphate, phosphate, maleate, ascorbate, acetate, citrate, benzoate, succinate, and tartarate salts. Dosage and design of administration regimen is well known to those skilled in the art.

The protein, or active fragments or variants thereof may be administered by standard routes. For example, routes of administration include oral, rectal, transmucosal, transdermal, or intestinal administration; parenteral delivery, including intramuscular, intravenous, subcutaneous, cutaneous, intramedullary injections, as well as intrathecal, direct intraventricular, intravenous, intraperitoneal, intranasal, or intraocular.

The human gene (G1h) is shown herein to have widespread distribution and activation patterns that suggest a broader range of activities and potential therapeutic and diagnostic utilities. Some states/conditions under which the expression of this gene is altered are discussed below:

Obesity and Diabetes

The human gene (G1h) is shown herein to be elevated in the blood of normal obese individuals compared to levels in lean people. This indicates that the gene is either involved in fat metabolism or responds to the general metabolic and inflammatory (obese individuals have elevations in many inflammatory genes in their blood) abnormalities found in obesity. G1h may become elevated in chronic inflammation as a counter regulatory mechanism to limit the cellular proliferation noted in blood vessels, adipocytes and other organs noted in obesity. Therapies such as antibodies or small molecules based on the structure of P1h may be useful in promoting normal fat metabolism or blocking the adverse biological effects of obesity. A diagnostic test that measures elevated levels of G1h in the serum of patients with obesity or diabetes may be a marker of increased risk of end-organ damage and tissue injury.

G1h levels in peripheral blood cells is inhibited in normal individuals during an oral glucose challenge and subsequent hyperglycemia. This indicates that G1h is responding acutely to states of glucose intolerance and hyperinsulinemia. This finding suggests that G1h is involved in the pathways of diabetes and/or its consequences. Targeting G1h or P1h with small molecules or mechanisms to maintain their function or quantities in cells or circulating concentrations, may prevent the cellular proliferation (neovascularization, atherosclerosis) noted in diabetes. Therapies targeting G1h such as RNA inhibitors may promote glucose tolerance.

Atherosclerosis

The human gene (G1h) is herein demonstrated to be present in endothelial cells and is downregulated in those cells following stimulation with Atrial Natriuretic Peptide 1 and tumor necrosis factor (TNF). These findings place G1h within the cells that play a key role in the pathogenesis of atherosclerosis and furthermore demonstrate that G1h is regulated by the proinflammatory signals that generate atherosclerosis. Since atherosclerosis is a proliferative lesion induced in part by microvascular injury to endothelial cells, G1h and consequently P1h may play a role in the pathogenesis of atherosclerosis. P1h may prevent the proliferation of smooth muscle cells and inflammatory cells into the sub-endothelial fatty streak that precipitates atherosclerosis. Atherosclerosis may be treated or alleviated by promoting the expression of G1h by viral vectors that encode for the gene or by identifying the signaling pathways that promote G1h expression. Alternatively, delivering the protein product as a recombinant protein may prevent or alleviate atherosclerosis.

Neurological Disorders

Despite the lack of typical immune cells such as lymphocytes and macrophages, the human G1h gene is herein shown to be highly expressed in the adult brain. This indicates that G1h is expressed in neural cells and may play an important role in maintaining the integrity of the central nervous system (CNS). This may be in the form of maintaining the blood/brain barrier thus limiting the ability to form a local immune reaction within the brain. Alternatively, G1h may regulate the proliferation of neural cells or their ability to synthesize key components of the CNS such as myelin. The latter function is suggested by the fact that G1h is absent in fetal tissues where myelin is generally absent. The enriched expression of G1h in human brain tissue suggests that G1h and subsequently P1h may play a critical role in recovery from neurological injury. Inhibiting G1h or P1h expression by means of small molecules, antibodies or receptor antagonists, may promote recovery from strokes and demyelinating disorders such as Guillian-Barre disease or multiple sclerosis.

Cardiac Disorders

Despite the lack of typical immune cells such as lymphocytes and macrophages, the human G1h gene is herein shown to be highly expressed in the adult heart. This indicates that G1h is expressed in cardiac cells and may play an important role in maintaining the integrity of the heart. G1h may regulate the proliferation of cardiac cells. The enriched expression of G1h in human heart tissue suggests that G1h and subsequently P1h may play a critical role in recovery from cardiac injury. Inhibiting G1h or P1h expression by means of small molecules, antibodies or receptor antagonists, may promote recovery from myocardial infarction or cardiac hypertrophy as observed in congestive heart failure and idiopathic cardiac hypertophic disorders. By inhibiting G1h and P1h by antibodies or small molecules, cardiac cells may proliferate at a greater extent following myocardial infarction maintaining cardiac function. Alternatively, patients with cardiac hypertrophy may benefit by promoting G1h expression or P1h therapy to block abnormal cardiac proliferation.

Cancer

The human G1h is present in elevated amounts in certain proliferating cancer cell lines. In human lung and prostate cancer cell lines, G1h is elevated greater than the housekeeping gene actin. On the other hand, in acute leukemic cells, colon cancer cells and chronic leukemic cells, G1h is downregulated. These results indicate that G1h is normally regulated in certain cancers and in others the anti-proliferative effect of G1h is somehow bypassed. Therefore, expression of G1h may be a marker for greater metastatic ability or a more aggressive cancer. G1h expression pattern may be useful as a diagnostic tool in characterizing the malignant potential of certain cancers as an aid to tailoring therapy. Alternatively, in cancers wherein G1h is downregulated therapy with G1h agonists or P1h protein may help in restoring a more normal growth pattern and reducing malignant potential. As an example, G1h expression may help differentiate more benign "growths", those with reduced G1h expression from more malignant "growths" those with high G1h expression.

Fetal Development

The human G1h gene is highly repressed in fetal bone marrow, brain and liver. This suggests that G1h and subsequently P1h play an important role in fetal development. The lack of the anti-proliferative gene G1h in fetal life may allow for cellular proliferation and differentiation that is required for normal fetal development. Abnormally elevated levels of G1h in fetal life may lead to fetal developmental abnormalities involving the CNS, hemotologic system or gastrointestinal and hepatic organs. A diagnostic test that measures G1h gene expression in amniotic fluids may aid in prenatal diagnosis of organ developmental abnormalities. Suppressing G1h expression by small molecules or antibodies may help prevent developmental abnormalities.

Transplantation/Immunosuppression

Current therapies for transplant rejection include (1) calcineurin inhibitors such as cyclosporin and tacrolimus (2) steroids and (3) mycophenolate mofetil which inhibits the synthesis of GTP. Calcineurin inhibitors act by blocking the transcription factor NFAT thus preventing the transcription of mRNA of a variety of cytokines including interleukin-2. However, calcineurin inhibitors also stimulate the transcription of the immunosuppressive cytokine, transforming growth factor beta (TGFβ). Indeed, a significant proportion of the immunsuppressive effects of calcineurin inhibitors is mediated through TGFβ. Similar to the effect seen with TGFβ we now demonstrate that the combination therapy of tacrolimus and mycophenolate mofetil leads to increased expression of G1h gene. These results suggest that immunosuppressive therapy including tacolimus and mycophenolate mofetil induce G1h expression. Given the potential immunosuppressive and anti-proliferative effect of P1h protein, it may be possible that the effects of immunosuppressive therapy are mediated through the P1h protein. Thus, therapies designed to increase G1h and P1h may prove to be immunosuppressive in of themselves and may be useful agents in preventing rejection, autoimmunity and inducing tolerance. Moreover, G1h inducing therapies with small molecules or P1h exogenous therapy may be less toxic, more potent and more specific for transplant rejection.

G1h levels in patients blood, urine or transplant biopsy samples may reflect the overall immunosuppressive state of the individual. A diagnostic test based on G1h levels may be used to more effectively treat patients after transplantation by allowing for more specific immunosuppressive dosing. Alternatively, G1h levels measured in the blood, tissue or urine may be used to derive novel immune therapies (chemicals or biologic reagents) based on their ability to promote or inhibit G1h expression.

Novel immune therapies may be designed based on the structure of P1h. Specifically designing mimics or antagonists (small molecules or biologics) based on the structure of P1h or parts of P1h may lead to novel immune therapies.

The compositions of the present invention may also be used for suppressing an immune response including an immune response to a self antigen. Accordingly, the compositions of the present invention may be used for treatment of allergic reactions.

The invention is further described by the following non-limiting illustrative examples.

EXAMPLE 1

Initial experiments focused on identifying the human gene homologue of the mouse gene. This was accomplished using the Human Genome Map and public search engines through NCBI. An initial search for the location and genomic sequence of the previously described mouse gene was performed using the Celera Mouse Genome Database. A single identity with the mouse gene was located on chromosome 11. Using this information, a search for the human homologous gene location was made using the NCBI web based HomoloGene search engine. A single homologous region on human chromosome 17 was found that mapped to a contiguous region, NT_010755.14. The chromosomal locations of the gene, mouse chromosome 11 and human chromosome 17 respectively, were found to be completely homologous. The mouse gene (G1B) was used as a query in a blast search of the NCBI human genome database to identify the chromosomal location and cDNA clones that encode a similar or exact human gene. A single partial match to the human genomic DNA sequence, NT_010755.14/Hs17_10912 and a single human cDNA clone from the IMAGE database, gi/28703893/gb/BC047435.1, was found. Once the human gene was identified, regulatory regions for this gene including promoter regions, TATA box and polyadelylation site, were established using web-based search tools (MatInspector, TFBind, Promoter Inspector). Potential protein(s) that could be encoded by the human gene and cDNA clone were determined by finding the open reading frames using the NCBI ORF Finder tool and the web-based DNA/RNA translation tool, ExPASSy.

In order to clone the human gene (G1h), specific nucleotide primers were designed that included specific restriction enzyme cut sites that could be used later for protein expression cloning. Specifically, the 5' forward primer incorporated a XhoI site GGACTCGAGATGACTAGAATCGACACGTGTGCG (SEQ ID NO:6) and the 3' reverse primer incorporated a HindIII site TGAAAGCTTCCTTAAGCTGCATGGCATCCAGAAGAGAA (SEQ ID NO:7). Conditions of the PCR reaction were anealing temperature 60° C. for 1 minute, melting temperature 94° C. for 30 seconds for 30 cycles. The resultant 260 base pair fragment was gel purified and cloned directly into the PCR4-TOPO vector (Invitrogen, Carlsbad, Calif.). Purified plasmid was obtained from transformed *E. coli*, directly sequenced to confirm that the incorporated sequence was identical with the original G1h gene and digested with XhoI and HindIII. The resultant insert was gel purified and ligated directly into the protein expression vector PRSET-A (Invitrogen). The resultant vector was transformed into Rosetta-gami *E. coli*, purified and sequenced to confirm that the G1h insert was identical with that found in the human genome database.

Human G1h is located on the long arm of the human chromosome 17 at 17q12. FIG. 1 depicts the genomic structure of G1h. The identification of a TATA box, polyadenylation site, unique promoter sites that confirm the genetic basis for functionality of this gene and the linkage to inflammation is unique to this application. G1h is a typical single exon human gene, which contains a consensus polyadenylation site required for mRNA transcription. Prior to the gene sequence lays an archetypical TATA box required for binding of transcription factors (proteins) and initiation of transcription. Just 5' or upstream of G1h is a STAT-1 binding site. STAT-1 is a transcription factor that is activated by the proinflammatory signal, gamma-interferon, and governs gene expression during immunological responses. The presence of a STAT-1 binding site strongly suggests that G1h is regulated during immune reactions and lies in the pathway of cell signaling mechanisms.

The nucleotide sequence of the region of the human gene G1h encoding for the P1h protein is provided below.

```
ATGACTAGAATCGACACGTGTGCGTGCGCACGCGTGTGCGTGTGT    (SEQ ID NO: 1)
GTGTTCATCTGTCTGCATGTGGATCAATTTCTTTTAGAAAATAATTTATTG
TATGATTTATTTTGGAGTTATATTCTGATTACAGTGCTCCCTCTCCCAAAT
AGCATTGATTTTTTCCCCCCTCTAAAATGTATAATCTGGTCTCAGGTTGG
ATTCTTTGGTACATTTCTCTCTTCTGGATGCCATGCAGCTTAA -
```

The amino acid sequence for the human protein is:

```
    MTRIDTCACARVCVCVFICLHVDQFLLENNLLYDLFWSYILITVLPLP    (SEQ ID NO: 2)
NSTDFFPPLKCIIWSQVGFFGTFLSSGCHAA -
```

FIG. 2 depicts the genetic similarity between the mouse P1B and the newly discovered human G1h. Significant similarities even identity are found in the beginning (5'), middle and ending (3') regions of the two genes.

FIGS. 3A and 3B show the amino acid sequence similarities between the human peptide P1h and mouse P1B peptide. Both genes are similar at 59% level and identical at 55% of the amino acids.

EXAMPLE 2

The following experiments demonstrate that the novel human gene G1h is expressed in normal human tissues. For these experiments, commercial mRNA samples (Origene Technologies, Rockville, Md.) were obtained that were isolated from various human tissues (FIG. 4). Expression of the human gene G1h is measured by PCR gene amplification. RNA samples at increasing concentrations were amplified using specific internal primers for G1h, 5' forward TAGAATCGACACGTGTGCGT (SEQ ID NO:8), and 3' reverse TGGCATCCAGAAGAGAGAAA (SEQ ID NO:9), and specific primers for beta actin, 5' forward GCATGGGTCAGAAGGAT (SEQ ID NO:10), and 3' reverse CCAATGGTGATGACCTG (SEQ ID NO:11). Conditions of the PCR reaction were anealing temperature 60° C. for 1 minute, melting temperature 94° C. for 30 seconds for 30 cycles. The concentration of mRNA that provided the most sensitive signal for G1h was used to compare the level of G1h between samples. The G1h and actin bands were scanned for intensity and the ratio of G1h signal to actin signal are reported. As shown in FIG. 4, human G1h gene is highly expressed (greater than one times that of actin) in human brain, heart, kidney, thyroid, adrenal, pancreas, skin and peripheral blood leukocytes. G1h is significantly repressed from colon, small intestine, placenta and bone marrow. Of note, G1h is absent or only modestly expressed in fetal brain, and liver. Thus, G1h is developmentally regulated; fetal tissues which undergo rapid cell divisions lack G1h or express it at extremely low levels. Organs that are highly protected from abnormal immune reactions such as the brain, pancreas, thyroid, adrenal and skin express high levels of G1h. Organs with a high innate reproductive capacity such as colon, small intestine, placenta and bone marrow lack G1h expression or express it at extremely low levels. These results indicate that G1h may have a role in controlling cell proliferation and/or local immunity.

EXAMPLE 3

Figure 5:
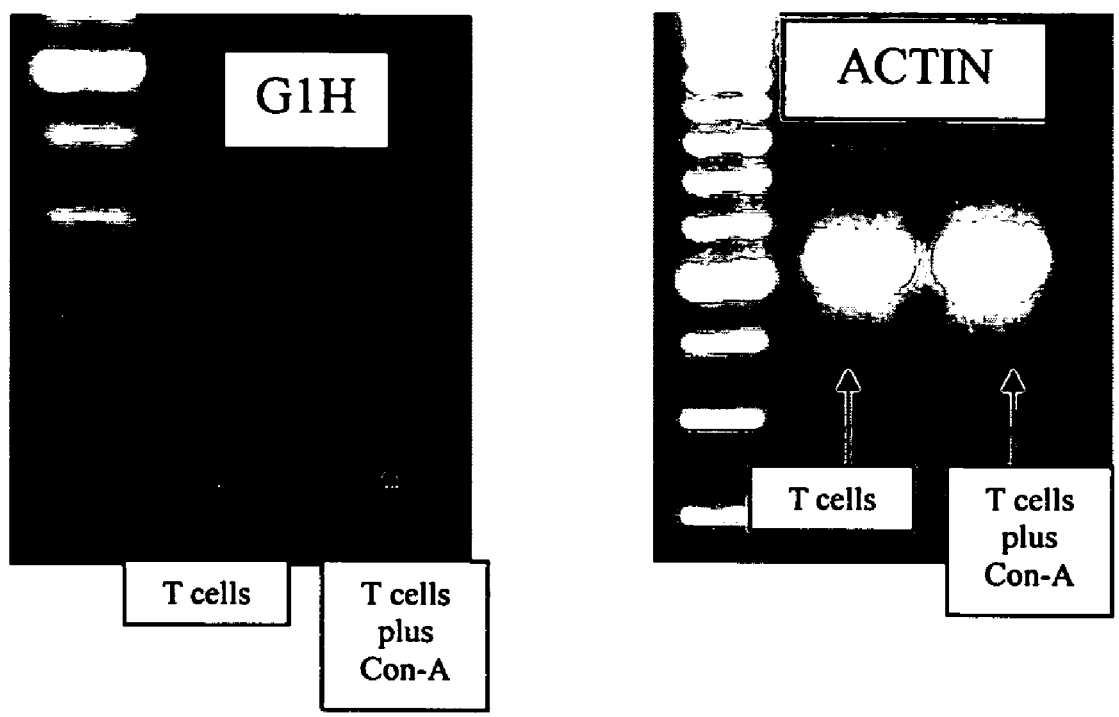
FIG. 5. Gene expression of human G1h in T lymphocytes following Con-A activation. Human G1h expression was examined using PCR techniques. Normal T lymphocytes were stimulated with Con-A at 5 µg/ml for 3 days, RNA were harvested and transcribed to cDNA. Both G1h and actin was amplified to 30 cycles using specific primers. Band densities were measured to calculate expression of both genes. Relative expression of G1h was calculated as the ratio of G1h density to that of actin.
Figure 6A:
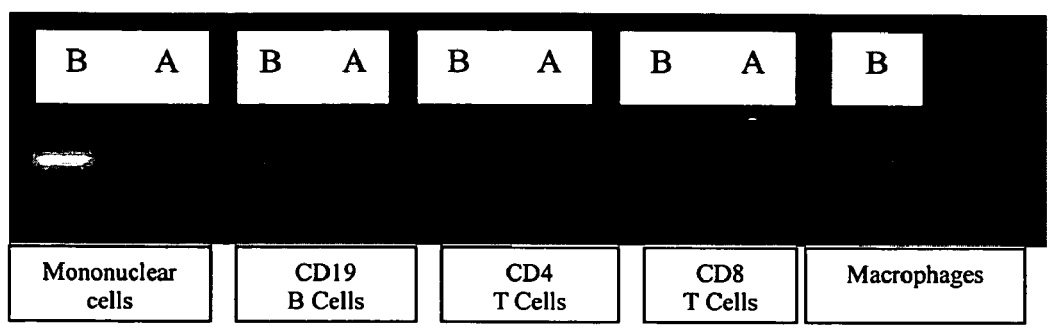
FIGS. 6A and 6B. Representation of the expression of human G1h in human peripheral blood leukocyte subsets before and after activation. For FIG. 6A, a panel of cDNA samples was commercially obtained from highly purified (>95%) cell populations before (B) and after (A) activation. T lymphocytes were activated by Con-A and B lymphocytes by phytohemagglutinin (PHA). In all cell subsets G1h expression decreases. For FIG. 6B, PCR techniques were used to determine G1h expression in peripheral leukocyte subsets. The results were normalized to actin. G1h expres sion was greatest in resting CD4 T cells and macrophages. Following stimulation, G1h expression diminished by 50 to 95% of baseline levels.
Figure 6B:
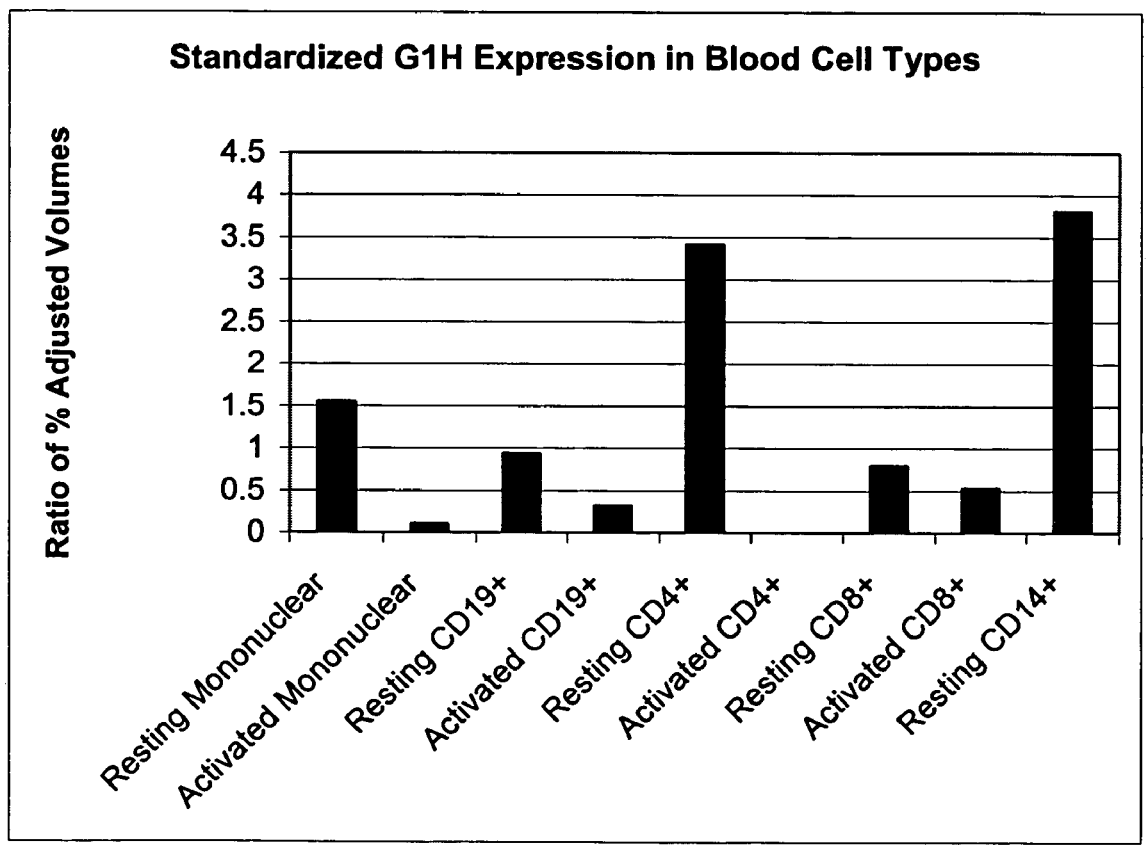

In the following experiments, the expression pattern of human G1h was examined in resting/proliferating cells. Human T cells were stimulated with concanalavin A (5 mcg/ml) in tissue culture for a period of 48 hours. RNA was harvested from resting T cells (control, unstimulated) and stimulated T cells using Qiagen kits for tissue culture samples. RNA was examined by RTPCR for expression of G1h and actin using primers and PCR conditions described previously for Origene experiments. The PCR cycle number was 27. The resultant PCR products were separated on agarose gels, stained with ethidium bromide and analyzed by densitometry using BioRad GelDoc 2000 systems. Results are provided as the ratio of G1h to beta actin. In normal resting human T lymphocytes, G1h is expressed at high levels (FIG. 5). Following activation with a non-specific T cell stimulation, concanavalin-A, expression of G1h decreases by approximately 30 to 40%. These results were confirmed and expanded using a commercially available panel of cDNA samples obtained from highly purified T lymphcyte subsets, B lymphocytes and macrophages (FIGS. 6A and 6B). The decrease in G1h expression was most prominent in CD4 T cells where G1h fell to less than 10% of baseline expression levels. These results suggest that G1h is related to cell activation and proliferation. Activated cells downregulate G1h expression which may allow progression through cell cycle.

EXAMPLE 4

Figure 7:
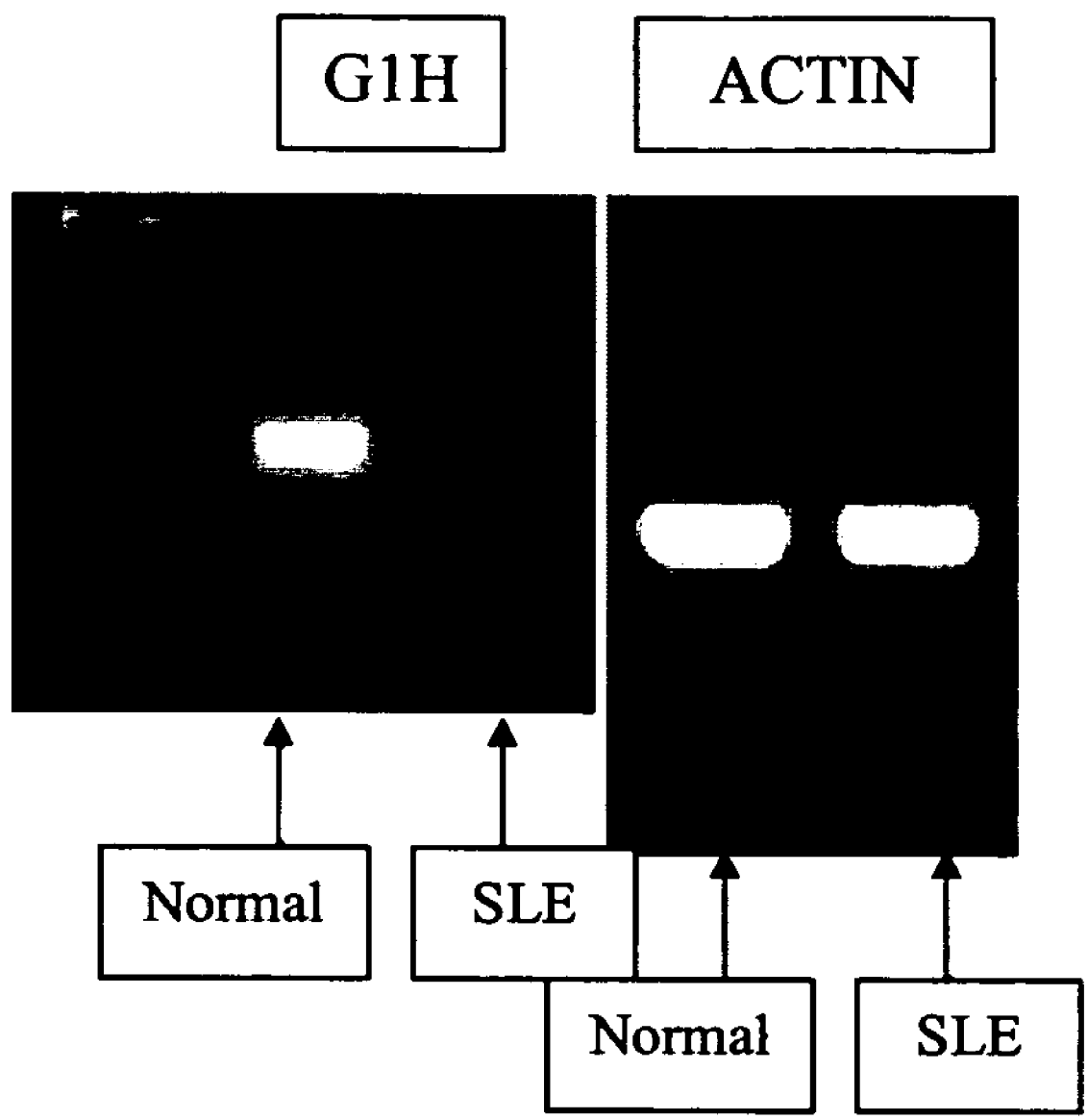
FIG. 7. Representation of G1h and Actin (housekeeping gene) expression in a patient with SLE and a normal patient. The patient with SLE has 49% lower expression than normal.

The in vivo relevance of G1h gene expression was examined in a patient suffering from systemic lupus erythematosus (SLE) (FIG. 7). In this experiment, G1h gene levels were determined in the peripheral blood cells (PBC) of a normal individual and a patient with SLE. Normal human PBC were obtained from a healthy volunteer and a female individual who was suffering from acute SLE as defined by arthritis, glomerulonephritis and fevers. The PBC were processed for RNA using Qiagen kits (QIAGEN mini-blood kit). The RNA was subjected to RTPCR using methods and primers previously described for beta actin and G1h. The PCR cycle number was 27. The resultant PCR products were separated on agarose gels, stained with ethidium bromide and analyzed by densitometry using BioRad GelDoc 2000 systems. Results are provided as the ratio of G1h to beta actin. Compared to normal G1h levels, the patient with SLE expressed 49% less G1h in peripheral blood leukocytes.

Given the fact that patients with SLE have a disorder characterized by polyclonal immune cell activation, this result suggests that G1h expression is downregulated in the cells affected by this autoimmune disorder. Thus, in human autoimmune disease G1h gene is abnormally regulated suggesting that treatment with G1h encoded protein may restore immunological balance and offer a unique cure for human autoimmunity.

EXAMPLE 5

Figure 8A:
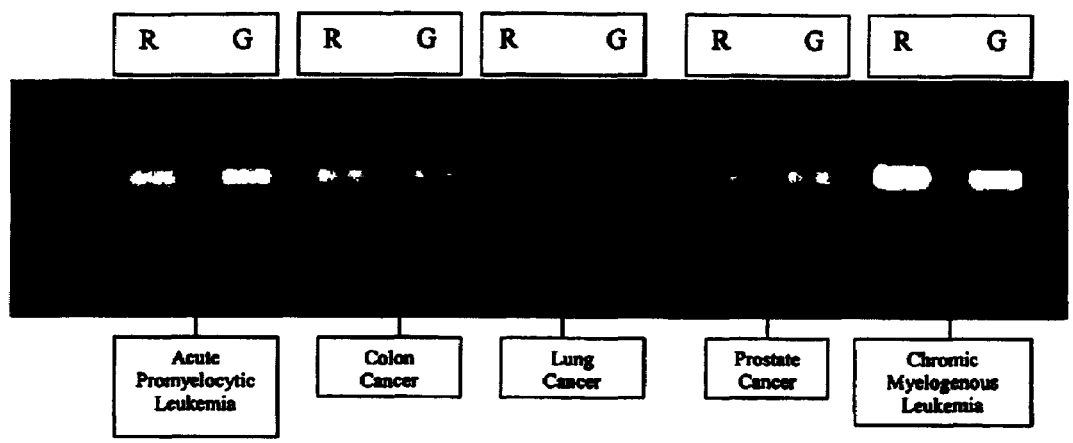
FIGS. 8A and 8B. Representation of G1h expression in cancer cell lines.
Figure 8B:
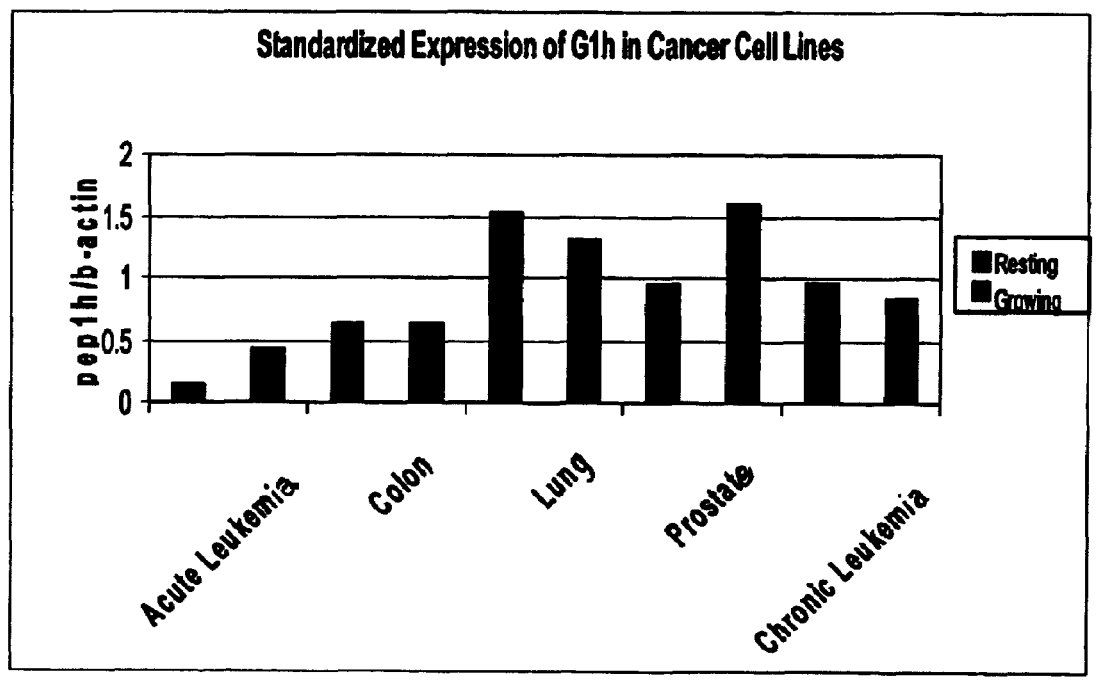

G1h expression was also examined in cancer cell lines. Human cancer cell lines studied for G1h expression included HL-60 (acute leukemia), LS174 (colon), A549 (lung), K562 (chronic myelocytic leukemia) and prostate (Du145). Individual cells were harvested for RNA at confluencey when growth was arrested (resting state) or at an exponential rate of growth (proliferating). Cells were grown in DMEM tissue culture media containing 10% fetal calf serum and hepes buffer using standard techniques. RNA was harvested using Qiagen kits as described and subjected to RTPCR using primers for beta actin and G1h as described. The PCR cycle number was 25. The resultant PCR products were separated on agarose gels, stained with ethidium bromide and analyzed by densitometry using BioRad GelDoc 2000 systems. Results are provided as the ratio of G1h to beta actin. In contrast to normal cells in which G1h expression was most prominent in the resting state and diminished or absent in the activated or proliferating state, proliferating cancer cell lines inherently express G1h (FIG. 8A). The level of G1h expression is determined as a ratio of actin expression (FIG. 8B). In these experiments, lung and prostate cancer cell lines expressed the highest levels of G1h relative to actin. Noteworthy, cancer cells did not express as high G1h levels as normal peripheral mononuclear cells. These results suggest that proliferating cancer cells either (1) overcome the growth inhibitory activity of the G1h gene (2) express high levels of G1h gene and, in turn, its protein product (P1h) thereby inhibiting surrounding cells and providing cancer cells a growth advantage or (3) produce P1h to induce a state of immunosuppression providing a means to escape immunosurveillance. Moreover, G1h is expressed preferentially in certain tumor cell lines. Therefore, the G1h gene may play an important role determining certain cancer biologic behaviors and may be a potential target for cancer therapy.

EXAMPLE 6

Figure 9:
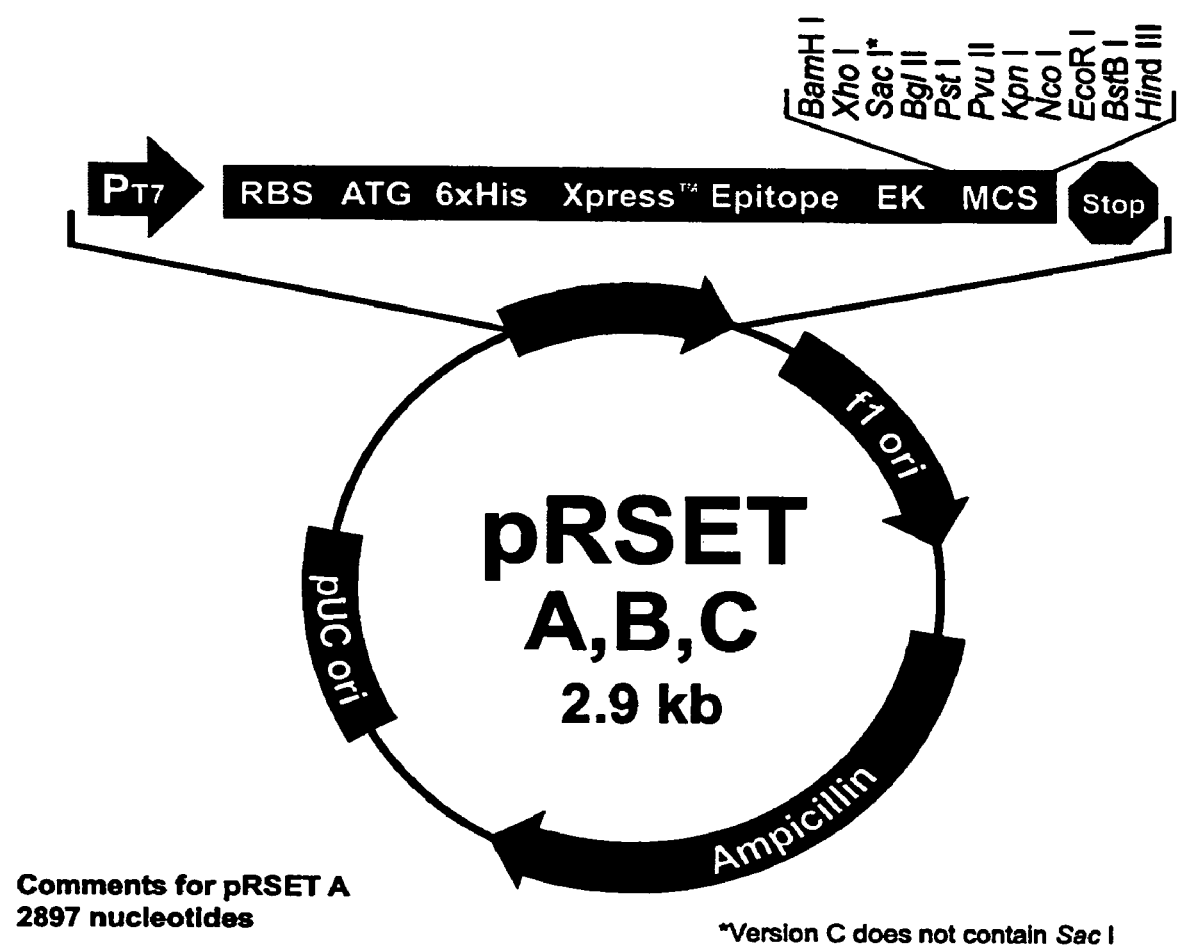
FIG. 9. The map of the PRSET DNA vector (2897 nucleotides) used to transform Rosetta-gammi *E. coli* bacteria to express human P1h and mouse P1B. The respective human (G1) and mouse gene were inserted into the multiple cloning site of the PRSET vector in frame as determined by direct sequencing (SEQ ID NO:3).

FIG. 9 shows the experimental strategy used to express recombinant P1h. The human P1h and mouse P1B proteins were synthesized in E. coli. In order to clone the human gene (G1h), specific nucleotide primers were designed that included specific restriction enzyme cut sites that could be used later for protein expression cloning. Specifically, the 5' forward primer incorporated a XhoI site GGACTCGAGAT-GACTAGAATCGACACGTGTGCG (SEQ ID NO:12) and the 3' reverse primer incorporated a HindIII site TGAAAGCTTCCTTAAGCTGCATGGCATC-
CAGAAGAGAGAA (SEQ ID NO:13). The template used for these reactions was the pCR-TOPO vector containing the correct G1h insert. Conditions of the PCR reaction were anealing temperature 60° C. for 1 minute, melting temperature 94° C. for 30 seconds for 30 cycles. The resultant 260 base pair fragment was gel purified and cloned directly into the PCR4-TOPO vector (Invitrogen, Carlsbad, Calif.). Purified plasmid was obtained from transformed E. coli, directly sequenced to confirm that the incorporated sequence was identical with the original G1h gene and digested with XhoI and HindIII. The resultant insert was gel purified and ligated directly into the protein expression vector PRSET-A (Invitrogen). The resultant vector was transformed into Rosetta-gami E. coli, purified and sequenced to confirm that the G1h insert was identical with that found in the human genome database. Sequence analysis also proved that the G1h gene was inserted in the correct "reading frame" that allows for protein synthesis. The G1h gene was isolated by PCR and inserted into the multiple cloning site within the PRSET vector (FIG. 9). This vector encodes for a peptide epitope "Express Epitope" that is recognized by a commercial antibody. This antibody can detect the expression of recombinant proteins by using Western Blot analysis. Furthermore, the PRSET vector encodes for 6 histidines that bind to nickel. This property can be exploited to isolate the recombinant protein using nickel column chromatography. The inserted genes were determined to be "in frame" by direct sequencing (SEQ ID NO:3). Transformed Rosetta-gami E. coli cells were grown and induced to express the recombinant proteins using IPTG.

Figure 10:
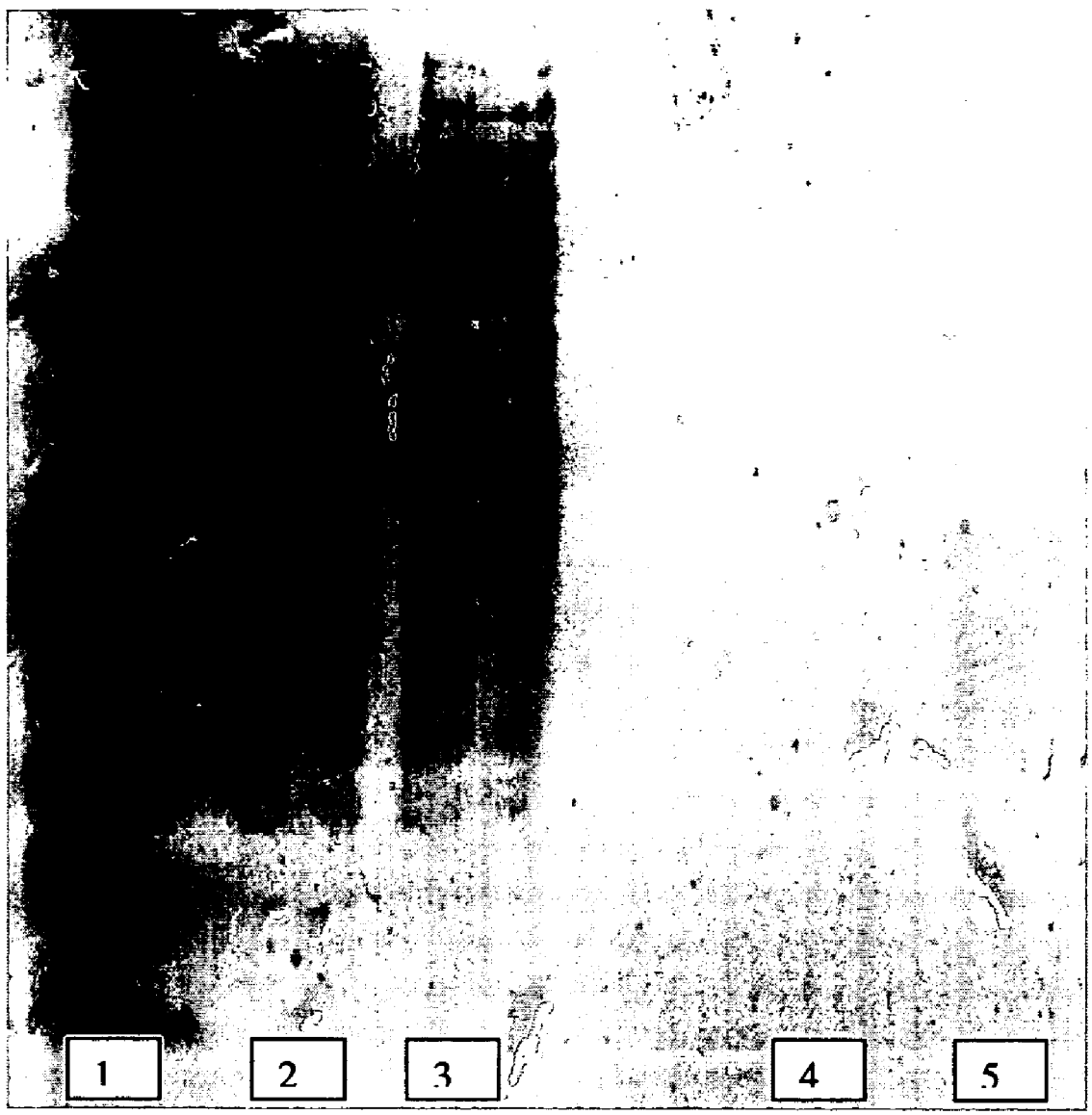
FIG. 10. Western blotting of protein lysates from transformed Rosetta-gami *E. coli* separated by PAGE. Lane 1: size markers. Lane 2: lysates isolated from P1B transformed *E. coli*. Lane 3: lysates isolated from P1h transformed *E. coli*. Lane 4: lysates purified by Nickel Chromatography from P1B transformed *E. coli*. Lane 5 lysates purified by Nickel Chromatography from P1h transformed *E. coli*.
Figure 11:
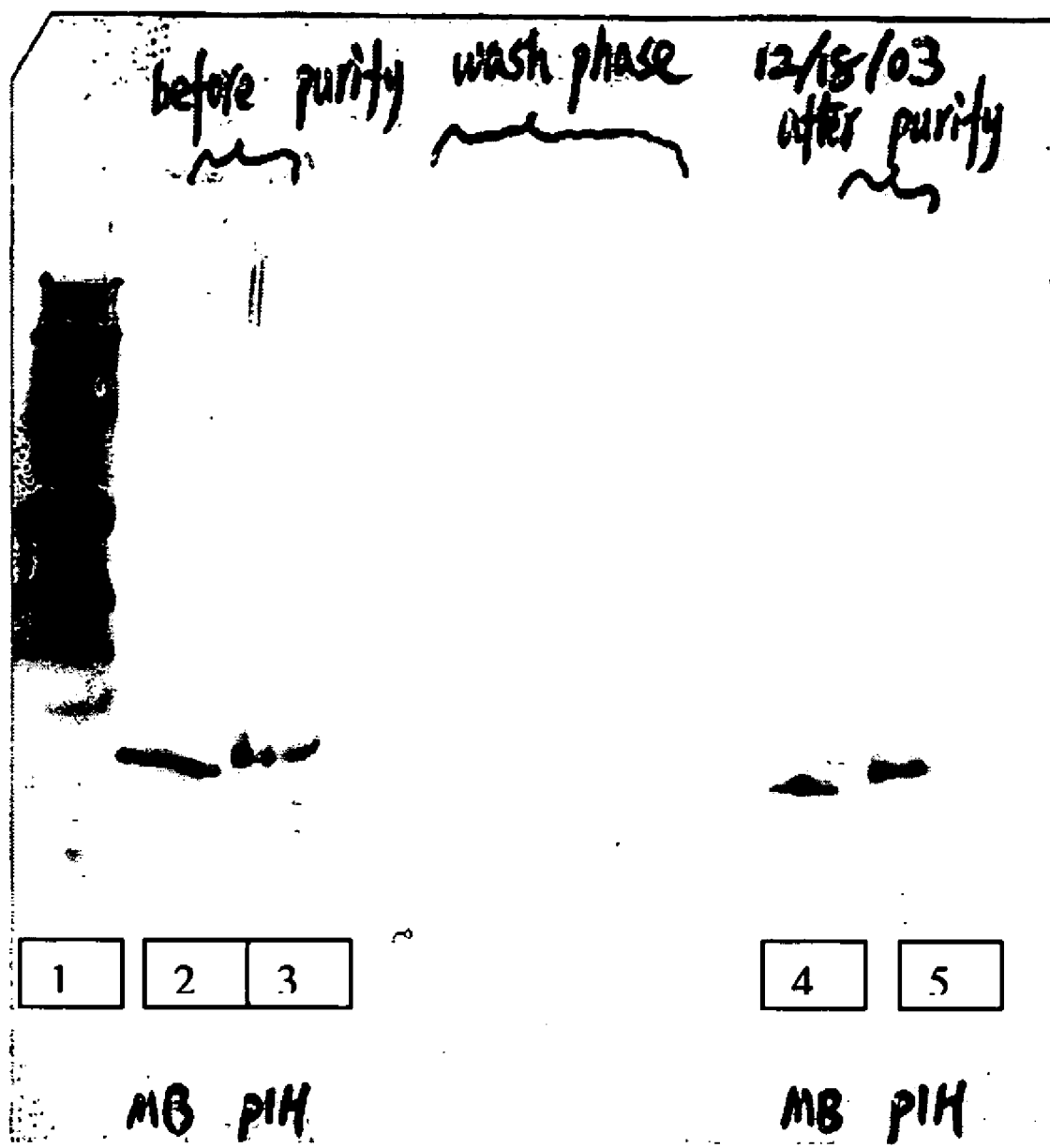
FIG. 11. Western blotting of protein lysates from transformed Rosetta-gami *E. coli* separated by PAGE and probed for expression of the "Express Epitope". Lane 1: size markers. Lane 2: lysates isolated from P1B transformed *E. coli*. Lane 3: lysates isolated from P1h transformed *E. coli*. Lane 4: lysates purified by Nickel Chromatography from P1B transformed *E. coli*. Lane 5: lysates purified by Nickel Chromatography from P1h transformed *E. coli*. The human fusion protein gene encodes for an 11 kDa protein (P1h) and the mouse gene encodes for a slightly smaller protein.

FIGS. 10 and 11 shows the PAGE gels of bacterial lysates before and after purification of P1h. The bacterial protein lysates were isolated and separated on standard PAGE gels. The same protein fractions were separated by PAGE, probed with an anti-"Express Epitope" antibody and detected by standard Western Blot techniques (FIG. 11). As shown in this figure both the human P1h and the mouse P1B are expressed in bacterial lysates as well as in the nickel pruified fraction. Both proteins are expressed at the correct molecular weight sizes. Therefore, both proteins are expressed in bacteria, albeit in small amounts, and bind to nickel as expected. The purified protein for P1h in lane 5 was used to test for biological function.

EXAMPLE 7

Figure 12:
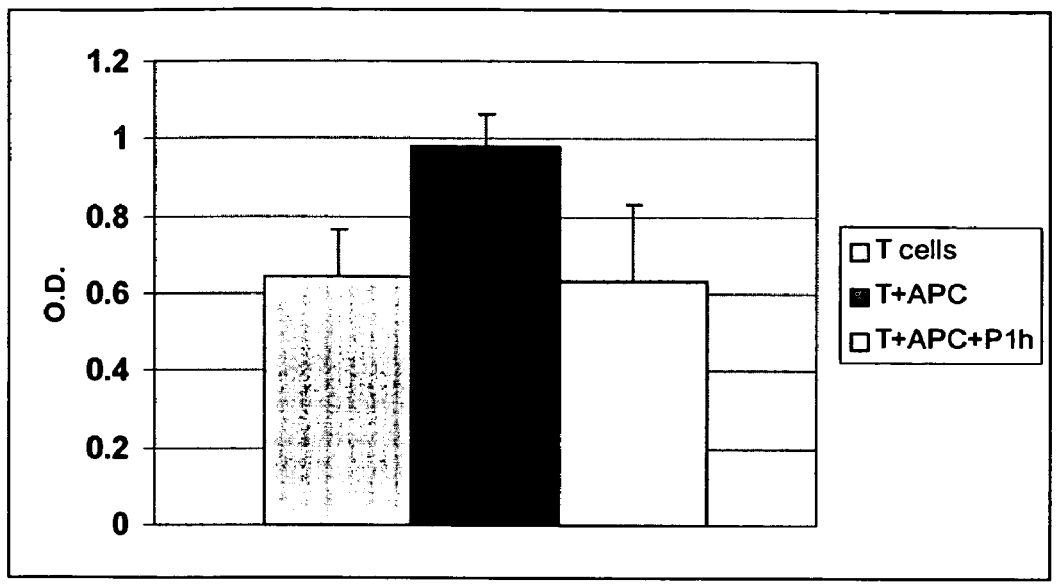
FIG. 12. Mixed lymphocyte reaction (MLR) was performed in 96 well plates adding either purified P1h, P1B and buffer to well at a dilution of 1:20. O.D. indicating T-cell levels are shown for the indicated groups. T cells in wells containing P1h proliferated to a greater extent that than controls (without additives), or those containing either P1B or buffer.
Figure 13:
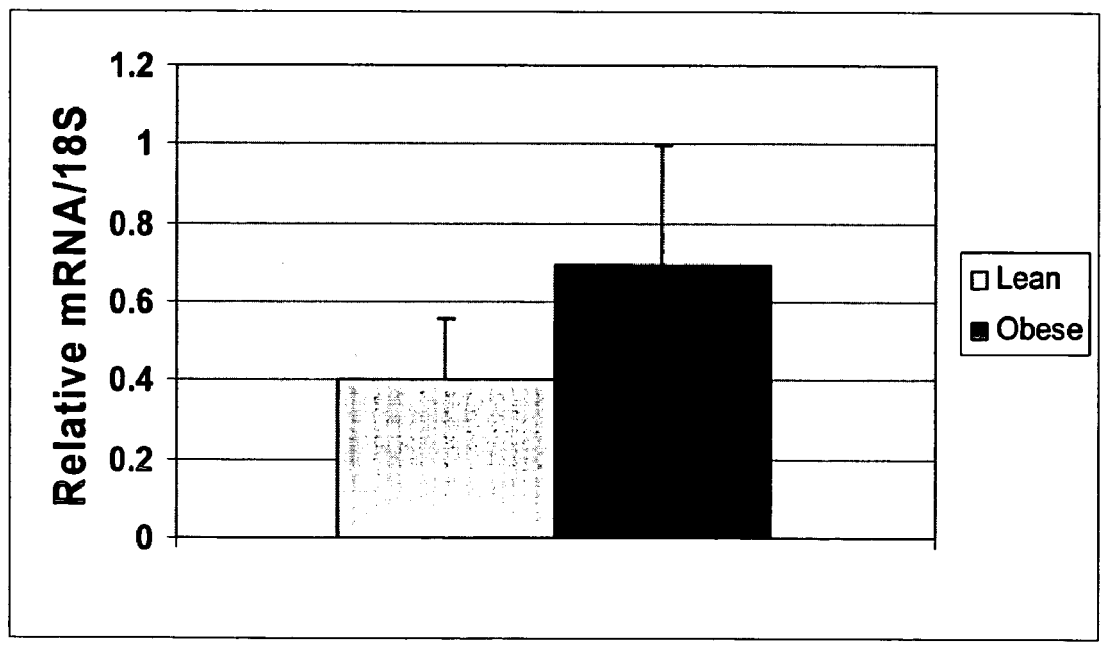
FIG. 13. Quantitative PCR (QPCR) results for RNA obtained from peripheral blood leukocytes (PBLs) isolated from obese and lean people. Obese people express 70% greater amounts of P1h gene in PBL's.

FIG. 12 depicts the in vitro bioassays determining the function of P1h. The functional assays used to test biological activity were mixed lymphocyte reactions (MLR). In these assays, purified T cells from one person are incubated in 96 well plates with irradiated peripheral white blood cells (PBL) from a different person. In response to HLA mismatches, the T cells proliferate. After 3 days, the individual wells are "developed" using color reagent and "read" on an ELISA plate reader. A higher optical density (OD) denotes the presence of more T cells indicating cell stimulation and proliferation occurred. Each well was performed in triplicate and results given in mean +/− standard deviation. Results from an MLR in which nickel purified P1h, P11B and buffer control were added to wells at a dilution of 1:20 (FIG. 13). T cells that were incubated with P1h proliferated to a lesser extent than those incubated with buffer alone and approached the proliferation noted in unstimulated T cells as controls. In this assay, P1h appears to specifically diminish the proliferation of human T cells in response to alloantigen.

EXAMPLE 8

In order to determine if P1h is regulated in other human illnesses, quantitative PCR assays were performed using specific primers for P1h in obese individuals compared to lean persons. All QPCR reactions were performed using a specific 5 prime primer AGGGAGCACTGTAATC (SEQ ID NO:14), 3 prime primer TGCATGTGGATCAATTTCTTT-TAGA (SEQ ID NO:15) and a FAM labeled reporter primer CCAACCTGAGACCAGATTATACATTTT (SEQ ID NO:16). QPCR was carried out in standard fashion using the Applied Biosystems method for multiplexing and standard 18S controls. Results are presented as fold-increase in signal compared to 18S standard. The resultant band is 146 nucleotides in length with a single band appearing on gel separation. FIG. 13 demonstrates that by quantitative PCR G1h is elevated in the PBC's of obese individuals compared to lean people. In order to determine if P1h is regulated in other human illnesses, quantitative PCR assays were performed using specific primers for P1h in obese individuals compared to lean persons. Obese individuals have 70% more gene expression in PBL's compared to lean people. This suggests that obesity may increase the expression of P1h which, in turn, may play an important role in the pathogenesis of this disorder. Furthermore, since Type 2 diabetes is a disorder of obesity, P1h may play an important role in the pathogenesis of this (Type 2 diabetes) major human illness.

EXAMPLE 9

Figure 14:
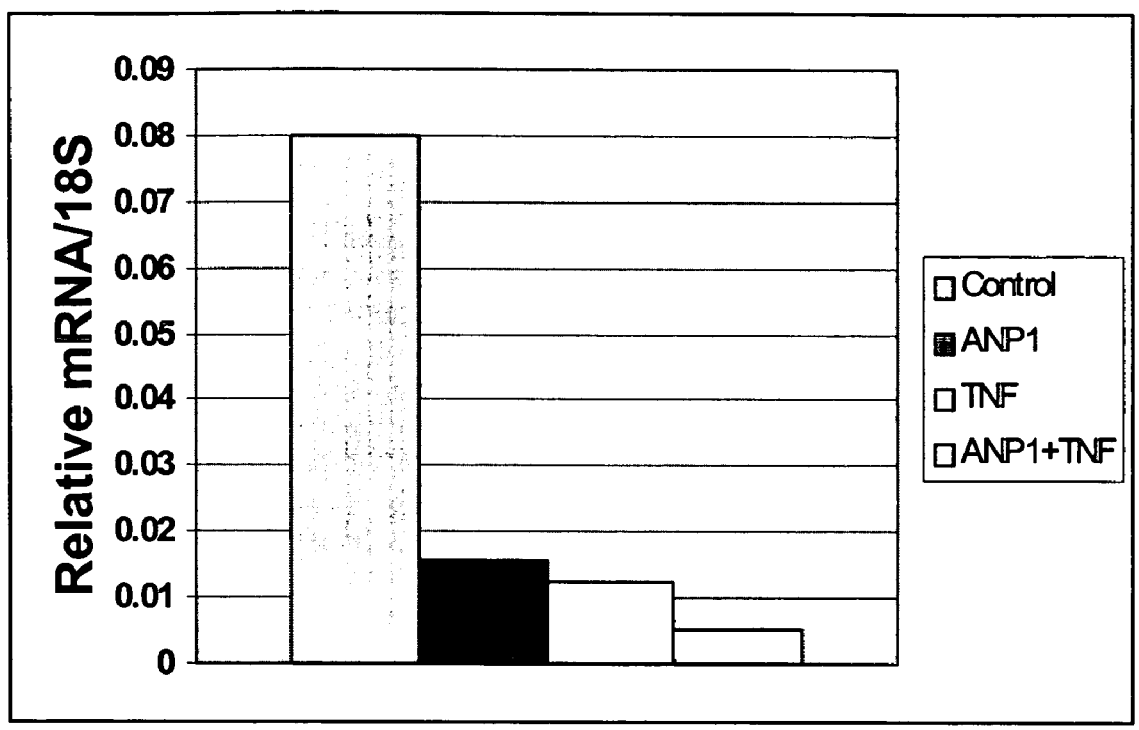
FIG. 14. Quantitative PCR (QPCR) results for RNA obtained from human endothelial cells in culture under control conditions and after stimulation with Atrial Natriuretic Peptide 1 (ANP1), Tumor Necrosis Factor (TNF) and a combination of ANP1+TNF. The relative amounts of mRNA encoding G1h was measured by comparison with the standard 18S RNA and compared amongst groups.

FIG. 14 demonstrates by QPCR that G1h is present in endothelial cells and is regulated by pro-inflammatory cytokines. QPCR was performed using methods and primers previously described in Example 8. Human endothelial cells were grown in tissue culture medium containing fetal calf serum. Total RNA was isolated from unstimulated endothelial cells or cells that were stimulated with tumor necrosis factor (TNF) or atrial natriuretic peptide (ANP). The RNA was reversed transcribed to cDNA and subjected to QPCR using techniques outlined above. Both TNF and ANP stimulation led to a marked decrease in G1h transcripts. These results suggest that the G1h gene and the encoded P1h protein may function in endothelial cells to maintain a resting state. Following stimulation, G1h levels fall as endothelial cells hypertrophy and differentiate. By stimulating G1h in endothelial cells by small molecules or by delivering the P1h protein exogenously, endothelial cells may remain quiescent and help prevent atherosclerosis or endothelial injury.

EXAMPLE 10

Figure 15:
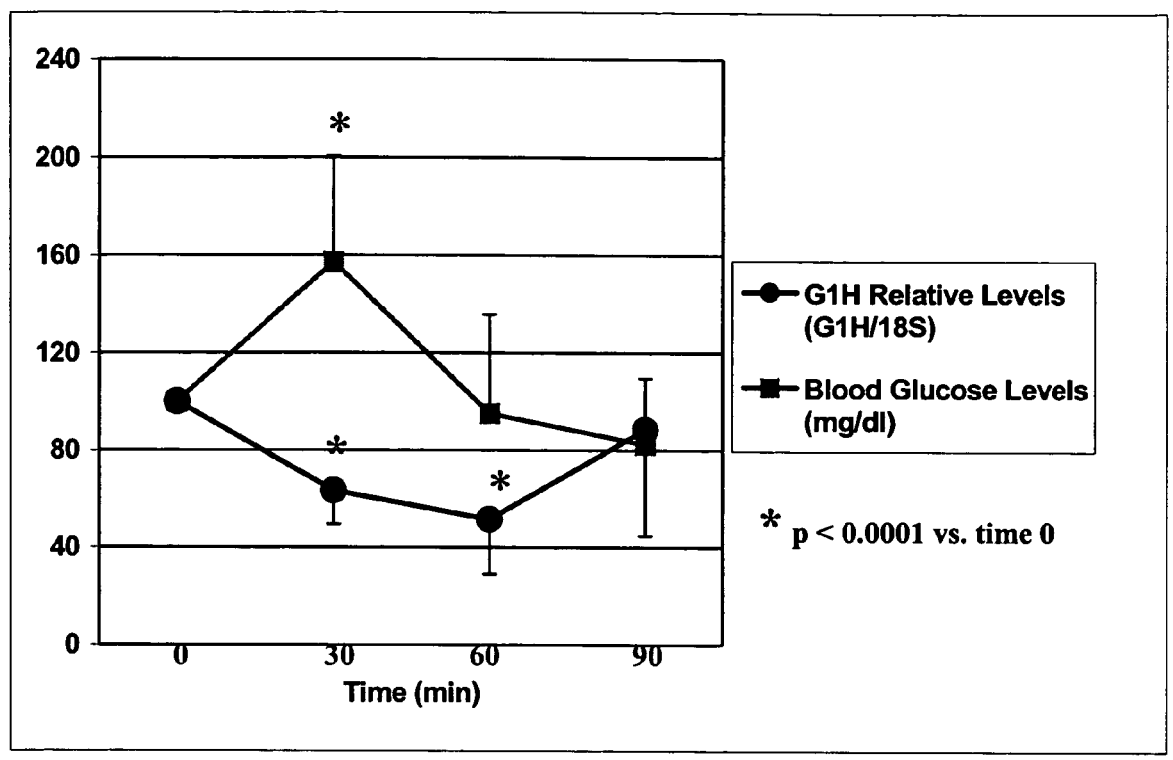
FIG. 15. Representation of G1h and blood glucose levels from five normal individuals subjected to a standard glucose tolerance test. Values are expressed as a function of time. Baseline levels of blood glucoses and G1h expression at time 0 are reported as 100. Subsequent changes are reported relative to the baseline. Normal individuals demonstrate a transient increase in blood glucose levels by 60% for 30 mins after which time the blood glucose returns to normal.

FIG. 15 demonstrates that G1h gene expression is regulated by hyperglycemia. G1h gene expression was determined by QPCR using techniques described in example 7 in PBC of normal individuals following an oral glucose challenge. Five normal individuals underwent a standard glucose tolerance test in which they ingested 75 grams of glucose containing solution at time 0. Blood samples were then drawn every 30 minutes for blood glucose determination and for total RNA extraction. The RNA was reverse transcribed to cDNA by standard methods and subjected to QPCR as described above. As shown in FIG. 15, following the ingestion of glucose, the blood sugar levels transiently increase. Concurrent with the increase in blood glucose levels, G1h expression in PBC's fall within 30 min and remain significantly depressed for 1 hour. Blood glucose levels return to normal under the influence of elevated insulin levels. G1h gene expression also returns to baseline following a 30 minute delay. These results indicate that G1h gene expression is involved in glucose metabolism and/or insulin signaling pathways. Given that hyperglycemia in diabetes is associated with cellular proliferation (neovascularization) and cellular differentiation, G1h and subsequently the P1h protein may play a significant role in the pathogenesis of diabetic complications. By removing the cellular proliferative block induced by G1h and P1h in resting cells, hyperglycemia may create a pro-proliferative environment by decreasing G1h and P1h concentrations. Therapeutic interventions based on strategies that promote G1h and/or P1h production may prevent diabetic complications. The relative levels of G1h in PBC of diabetic patients may be used as a marker to assess the relative risk of developing complications furthering the care of these patients.

EXAMPLE 11

Figure 16:
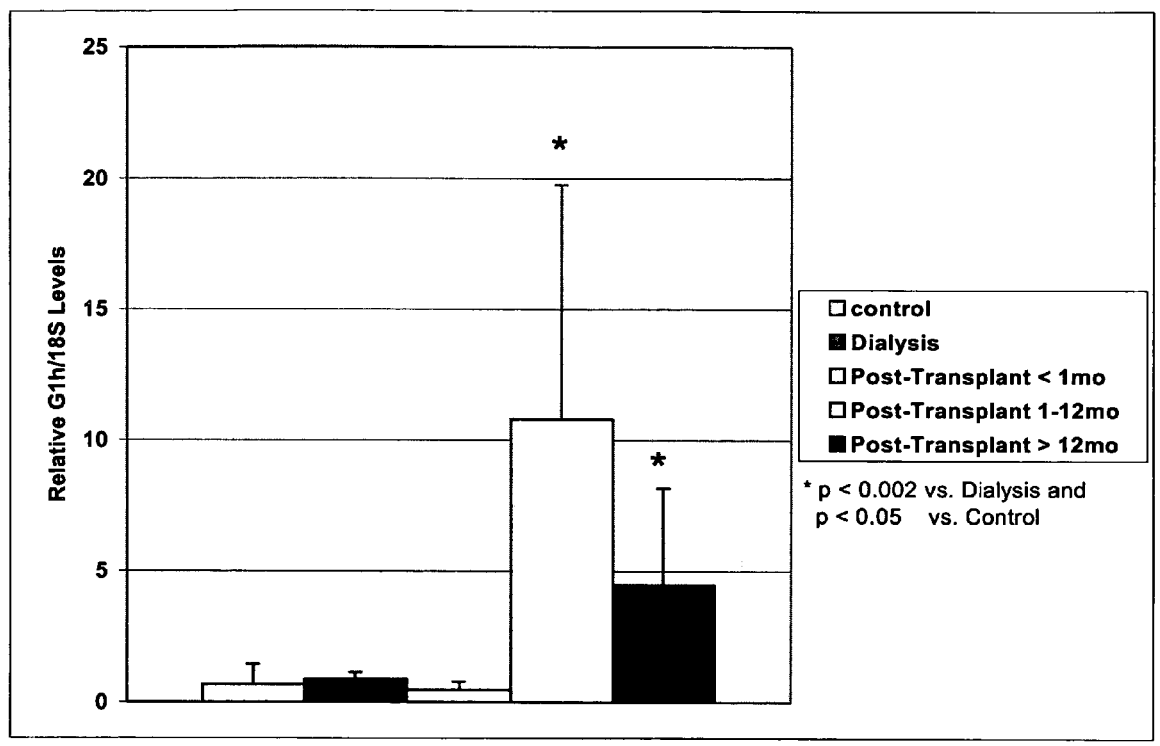
FIG. 16. QPCR results for G1h on blood samples obtained from normal subjects (n=3), dialysis patients (n=13), post-renal transplant patients who were less than one month post-transplant (n=2), between one and 12 months post-transplant (n=8) and more than 12 months after transplant (n=7). All transplant patients were treated with a combination of tacrolimus, mycophenolate mofetil and prednisone. Results are given as fold increase relative to the standard or "housekeeping" gene, 18S.

FIG. 16 demonstrates that the G1h gene is activated by immunosuppressive therapy following transplantation. In order to examine if G1h is regulated by kidney failure, dialysis therapy or following kidney transplantation, the PBC were collected from various groups of patients and the mRNA was subjected to QPCR techniques previously described in Example 7 for G1h and 18S expression. In normal controls (n=2) and in stable dialysis patients undergoing hemodialysis (n=13), the level of G1h gene expression is not elevated relative to 18S. Therefore, kidney disease and hemodialysis, which are states of chronic inflammation with elevations in many cytokines and growth factors, do not affect baseline G1h gene transcription. In contrast, the PBC of patients more than one month following transplantation and the introduction of immunosuppressive therapy express very high levels of G1h mRNA. These results suggest that immunosuppressive therapy including tacolimus and mycophenolate mofetil increases G1h expression. Given the potential immunosuppressive and anti-proliferative effect of P1h protein, it may be possible that the effects of immunosuppressive therapy are mediated through the P1h protein. Thus, therapies designed to increase G1h and P1h may prove to be immunosuppressive in of themselves and may be useful agents in preventing rejection, autoimmunity and inducing tolerance. Moreover, G1h inducing therapies with small molecules or P1h exogenous therapy may be less toxic, more potent and more specific for transplant rejection.

EXAMPLE 12

Figure 17A:
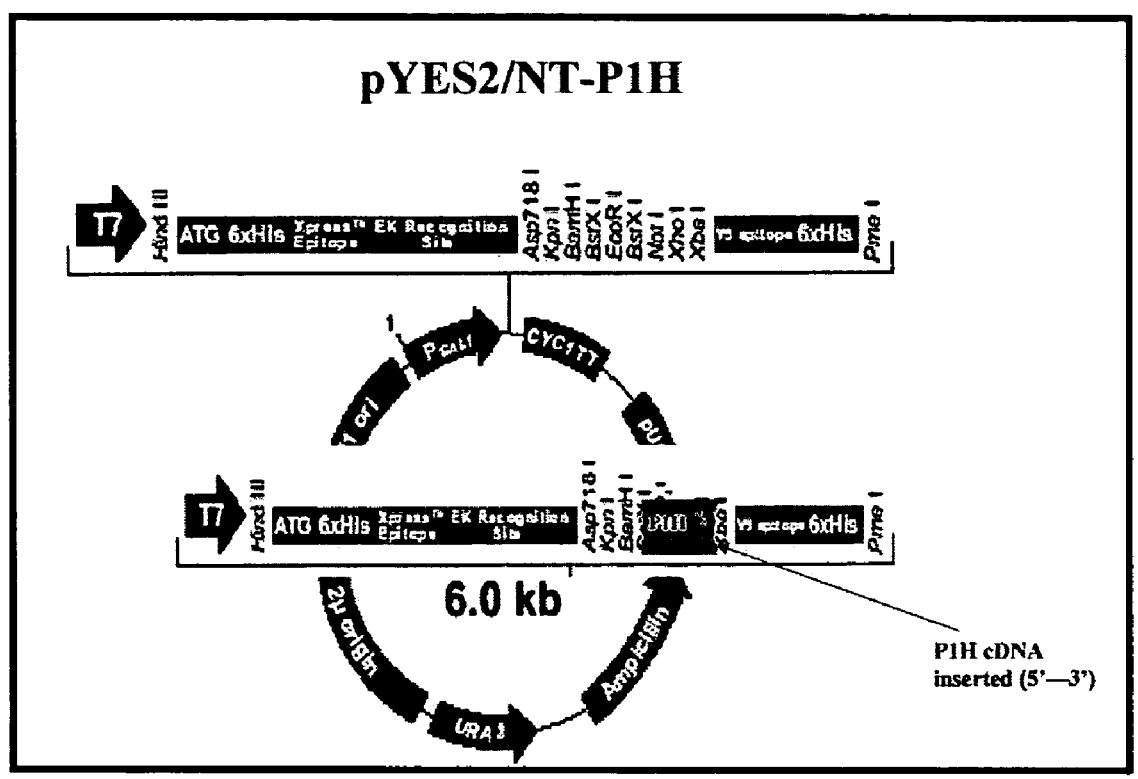
FIG. 17A is a representation of the map of Yeast Expression Vector. The gene G1h was amplified using the PRSET vector with EcoR1 restriction sites on both the 5' and 3' ends. The PCR product was directly cloned into the TOPO vector from which it was subsequently removed using EcoR1. The pYES/NT vector was linearized using EcoR1. The G1h DNA was inserted into the pYES/NT vector using standard techniques.

In this embodiment, the in vivo properties of recombinant P1h were tested in a mouse model of T cell mediated immunity. P1h synthesis was accomplished in yeast cells. Briefly, the gene, G1h, coding for P1h was cloned into a yeast expression vector, pYES2/NT. This vector was commercially purchased through Invitrogen and the gene encoding P1h was inserted into the polylinker region using EcoR1 sites. The map of the expression vector is shown in FIG. 17A.

Figure 17C:
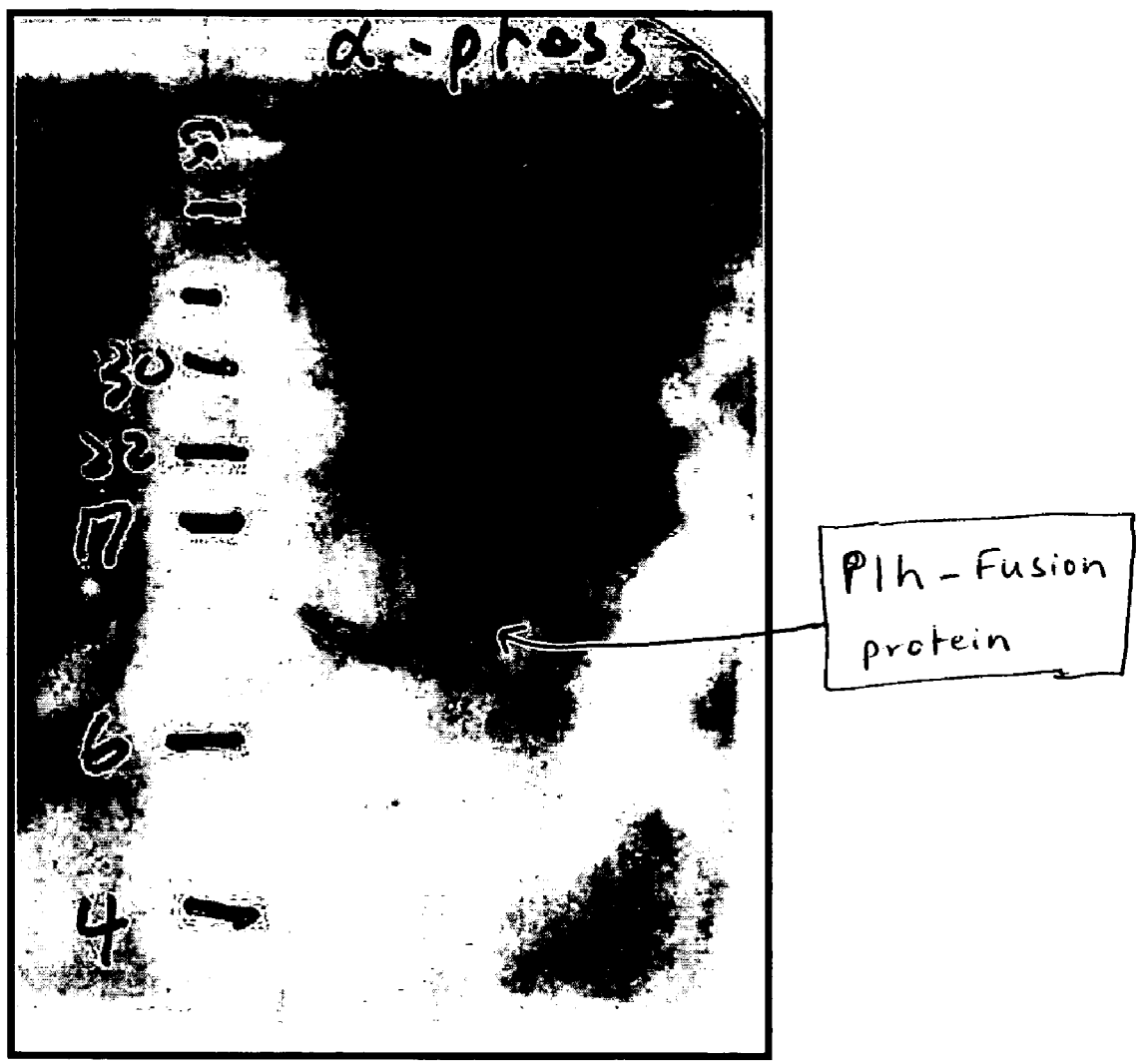
FIG. 17C is a representation of a Western blot for P1h-fusion protein. The nickel purified protein fraction was separated on a SDS PAGE gel and transferred to nitrocellulose paper. Following standard techniques, the paper was interacted with a commercially available antibody to the His-tag fusion partner. The presence of P1h-fusion protein was established by a second antibody technique that detected the bound anti-His antibody. The paper was developed on radiographic film. The predicted molecular weight of P1h-fusion protein is 14,000 Da and the band detected calculates to 13,800 Da.
Figure 17D:
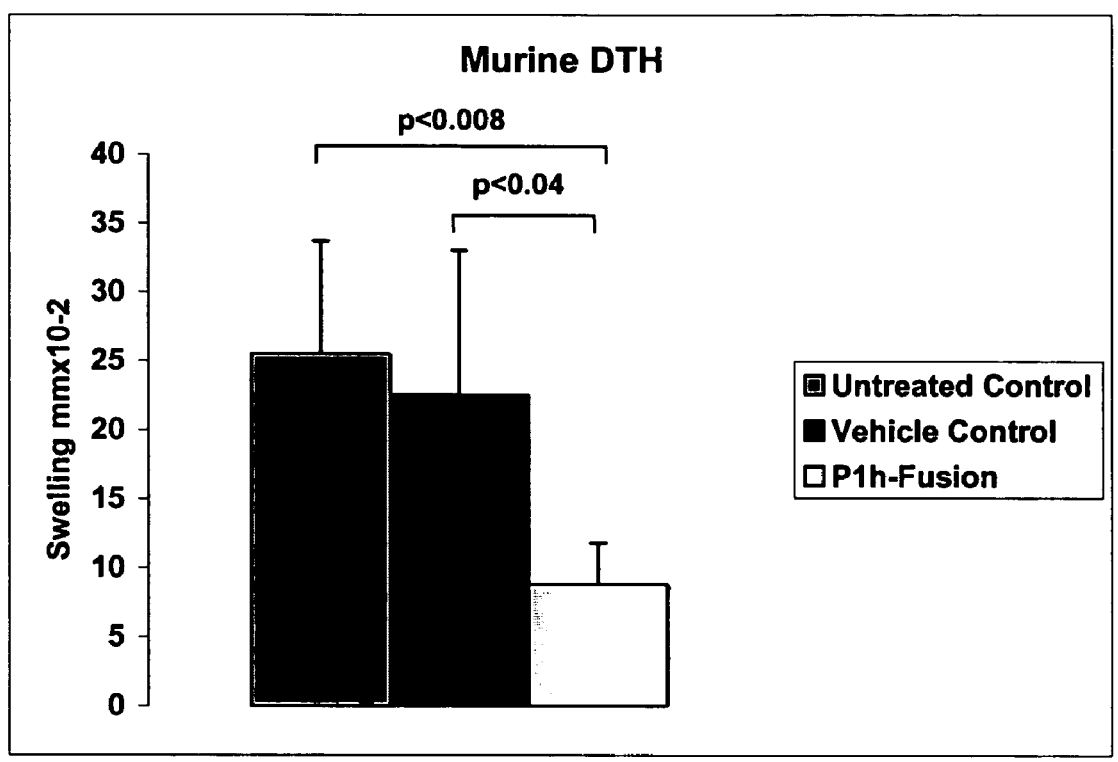
FIG. 17D is a representation of delayed type hypersensitivity reaction (DTH) experiment using P1h-fusion protein. Results are given as the difference in ear swelling between the Left "normal" ear and the Right "FITC challenged" ear. Units of swelling are measure in mm$\times 10^{-2}$.

Colonies of transformed yeast cells were harvested and the inserted vectors were sequenced. The vector sequence was confirmed and shown in FIG. 17B (SEQ ID NO:17). Yeast cells containing sequenced-confirmed vectors were induced to express the P1h fusion protein. Induced yeast cells were harvested, disrupted and proteins were extracted by standard means. The P1h fusion protein was then purified from the protein mixture by nickel column chromatography. Purified P1h fusion protein was soluble and its presence was confirmed by Western Blot (FIG. 17C). Contaminating proteins were minimal since on the Coomasie stained gel neither P1h nor other proteins were visualized. Larger molecular weight proteins may represent dimers of P1h-fusion proteins.

The in vivo effects of this purified P1h-fusion protein was tested in a mouse model of delayed type hypersensitivity reaction (DTH). This allergic reaction depends on immune reactivity mediated by CD4 T-helper cells and production of cytokines. The DTH was performed using a chemical, FITC, according to the methods outlined in Current Protocols in Immunology pages 4.2.1-4.2.5 and Tamaki, T. et. al. In J. Invest. Dermatology 76(4):275-278. Briefly, three groups of four Balb/c male mice were sensitized to FITC by cutaneous application. The first, control (C), group were untreated and one week later were challenged by re-application of FITC on the right ear. The second, vehicle control (VC), group were treated 30 minutes prior to the FITC sensitization and ear challenge with vehicle dissolved 1:2 dilution in dimethylsulfoxide (DMSO). The DMSO acts as a skin penetrating solution to deliver the vehicle or P1h-fusion locally. The third, experimental (E), group were treated with P1h-fusion protein dissolved in DMSO in a 1:2 dilution 30 minutes prior to application and challenge with FITC.

Twenty four hours after FITC challenge, the degree of swelling in the right ear (R-ear) was measured and compared to the left ear (L-ear). The difference in ear thickness defines the degree of inflammation and immune reactivity. Results of this 25.5+/−8.2 vs. 22.5+/−10.5 in vehicle controls vs. 8.8+/−3.0 in P1h-fusion protein treated mice.

These results demonstrate that recombinant, soluble purified P1h protein has in vivo effects that are immunosuppressive in nature. Moreover, these effects can be elicited by topical administration alleviating the need for systemic drug dispensation.

While this invention is described through specific embodiment, routine modifications will be apparent to those skilled in the art. Such modifications are intended to be within the scope of this invention.

The invention claimed is:

1. An isolated peptide comprising an amino acid sequence of SEQ ID NO:2.

2. A method for identifying altered expression of a human gene (G1h) in a human tissue, blood, urine or amniotic fluid sample comprising the steps of detecting the level of a polynucleotide encoding the peptide of SEQ ID NO:2 and comparing said level to the level in a sample from a matched normal tissue, blood, urine or amniotic fluid.

3. The method of claim 2, wherein the sample comprises peripheral blood cells.

4. The method of claim 3, wherein the peripheral blood cells are T-lymphocytes.

5. The method of claim 3, wherein the peripheral blood cells are obtained from a patient diagnosed with systemic lupus erythematosus.

6. The method of claim 2, wherein the sample comprises endothelial cells.

7. The method of claim 2, wherein the sample comprises malignant cells.

8. The method of claim 2, wherein the sample comprises amniotic fluid.

9. A method for suppressing the immune response in an individual, comprising the steps of administering a composition comprising a therapeutically effective amount of a polypeptide of SEQ ID NO:2, wherein the immune response is suppressed after the administration of the peptide.

10. The method of claim 9, wherein the polypeptide is administered by a method selected from the group consisting of topical, oral, rectal, transmucosal, intestinal intramuscular, transdermal, subcutaneous, cutaneous, intramedullary injections, intrathecal, intraventricular, intravenous, intraperitoneal, intranasal and intraocular.

11. The method of claim 9, wherein the polypeptide is administered topically.

12. The method of claim 9, wherein the immune response is generated in response to a self-antigen.

13. The method of claim 9, wherein the immune response is an allergic reaction.

* * * * *

SEQUENCE LISTING

```
<160> NUMBER OF SEQ ID NOS: 17

<210> SEQ ID NO 1
<211> LENGTH: 240
<212> TYPE: DNA
<213> ORGANISM: Homo sapiens
<220> FEATURE:

<400> SEQUENCE: 1
atgactagaa tcgacacgtg tgcgtgcgca cgcgtgtgcg tgtgtgtgtt              50
catctgtctg catgtggatc aatttctttt agaaaataat ttattgtatg             100
atttattttg gagttatatt ctgattacag tgctccctct cccaaatagc             150
attgattttt tcccccctct aaaatgtata atctggtctc aggttggatt             200
ctttggtaca tttctctctt ctggatgcca tgcagcttaa                        240

<210> SEQ ID NO 2
<211> LENGTH: 79
<212> TYPE: PRT
<213> ORGANISM: Homo sapiens
<220> FEATURE:

<400> SEQUENCE: 2

Met Thr Arg Ile Asp Thr Cys Ala Cys Ala Arg Val
 1               5                  10

Cys Val Cys Val Phe Ile Cys Leu His Val Asp Gln
        15                  20

Phe Leu Leu Glu Asn Asn Leu Leu Tyr Asp Leu Phe
25                  30                  35

Trp Ser Tyr Ile Leu Ile Thr Val Leu Pro Leu Pro
            40                  45

Asn Ser Ile Asp Phe Phe Pro Pro Leu Lys Cys Ile
    50                  55                  60

Ile Trp Ser Gln Val Gly Phe Phe Gly Thr Phe Leu
                65                  70

Ser Ser Gly Cys His Ala Ala
        75

<210> SEQ ID NO 3
<211> LENGTH: 959
<212> TYPE: DNA
<213> ORGANISM: artificial sequence
```

<220> FEATURE:
<223> OTHER INFORMATION: the PRSET DNA vector containing the coding sequence for the P1h. The coding region of the P1h is from 170-409

<400> SEQUENCE: 3

| | | |
|---|---|---|
| cacggtttcc tctagaaata attttgttta actttaagaa ggagatatac | 50 |
| atatgcgggg ttctcatcat catcatcatc atggtatggc tagcatgact | 100 |
| ggtggacagc aaatgggtcg ggatctgtac gacgatgacg ataaggatcg | 150 |
| atggggatcc gagctcgaga tgactagaat cgacacgtgt gcgtgcgcac | 200 |
| gcgtgtgcgt gtgtgtgttc atctgtctgc atgtggatca atttcttta | 250 |
| gaaaataatt tattgtatga tttattttgg agttatattc tgattacagt | 300 |
| gctccctctc ccaaatagca ttgattttt ccccctcta aaatgtataa | 350 |
| tctggtctca ggttggattc tttggtacat ttctctcttc tggatgccat | 400 |
| gcagcttaag gaagcttgat ccggctgcta acaaagcccg aaaggaagct | 450 |
| gagttggctg ctgccaccgc tgagcaataa ctagcataac cccttggggc | 500 |
| ctctaaacgg gtcttgaggg gttttttgct gaaaggagga actatatccg | 550 |
| gatctggcgt aatagcgaag aggcccgcac cgatcgccct tcccaacagt | 600 |
| tgcgcagcct gaatggcgaa tgggacgcgc cctgtagcgg cgcattaagc | 650 |
| gcggcgggtg tggtggttac gcgcagcgtg accgctacac ttgccagcgc | 700 |
| cctagcgccc gctcctttcg ctttcttccc ttcctttctc gccacgttcg | 750 |
| ccggctttcc ccgtcaagct ctaaatcggg gctccctt agggttccga | 800 |
| tttagtgctt tacggcacct cgaccccaaa aaacttgatt agggtgatgg | 850 |
| ttcacgtagt gggccatcgc cctgatagac ggttttcgc cctttgacgt | 900 |
| tggagtccac gttctttaat agtggactct tgttccaaac tggaacaaca | 950 |
| ctcaaccct | 959 |

<210> SEQ ID NO 4
<211> LENGTH: 36
<212> TYPE: PRT
<213> ORGANISM: mus musculus
<220> FEATURE:

<400> SEQUENCE: 4

Met Cys Ala Cys Val Cys Pro Ser Ala Cys Ala Ser
            5                   10

Val Ser Leu Lys Asn Asn Leu Leu Cys Asp Phe Leu
        15                  20

Trp Ser Phe Cys Ser Gly Tyr Ser Ala Ala Pro Gln
25              30                  35

<210> SEQ ID NO 5
<211> LENGTH: 600
<212> TYPE: DNA
<213> ORGANISM: homo sapiens
<220> FEATURE:

<400> SEQUENCE: 5

| | | |
|---|---|---|
| aaaaaggata actttaaccg aaggaagggt ttggttccat tcaactccac | 50 |
| attcattgtg cctttacttg cattagattt ctgtgctttc ttcctttccc | 100 |
| tctttgaagc aattaaaatc ttccttgata actgctgttt ctttctactc | 150 |

-continued

| | |
|---|---|
| ttgtttctgg caatttagtg ggttccttct ctagtggtct taaatctcat | 200 |
| tccactggtg gcaagatggg gcctagcctt cttttcacat gtctaatctt | 250 |
| ttcctttctc atggtgccct ccatggaagt cacagtcaac actgaataaa | 300 |
| tgactagaat gacacgtgtg cgtgcgcacg cgtgtgcgtg tgtgtgttca | 350 |
| tctgtctgca tgtccatcaa tttcttttag aaaataattt attgtatgat | 400 |
| ttattttgga gttatattct gattacagtg ctccctctcc caaatagcat | 450 |
| tgattttttc cccctctaa aatgtataat ctggtctcag gttggattct | 500 |
| ttggtacatt tctctcttct ggatgccatg cagcttaatt aaaaccttgc | 550 |
| ttaaaaacaa aaagtgaaaa ttgtgtactc ttgtctggaa taccgcctca | 600 |

<210> SEQ ID NO 6
<211> LENGTH: 33
<212> TYPE: DNA
<213> ORGANISM: artificial sequence
<220> FEATURE:
<223> OTHER INFORMATION: PCR primer

<400> SEQUENCE: 6

| | |
|---|---|
| ggactcgaga tgactagaat cgacacgtgt gcg | 33 |

<210> SEQ ID NO 7
<211> LENGTH: 40
<212> TYPE: DNA
<213> ORGANISM: artificial sequence
<220> FEATURE:
<223> OTHER INFORMATION: PCR primer

<400> SEQUENCE: 7

| | |
|---|---|
| tgaaagcttc cttaagctgc atggcatcca gaagagagaa | 40 |

<210> SEQ ID NO 8
<211> LENGTH: 20
<212> TYPE: DNA
<213> ORGANISM: artificial sequence
<220> FEATURE:
<223> OTHER INFORMATION: PCR forward primer

<400> SEQUENCE: 8

| | |
|---|---|
| tagaatcgac acgtgtgcgt | 20 |

<210> SEQ ID NO 9
<211> LENGTH: 20
<212> TYPE: DNA
<213> ORGANISM: artificial sequence
<220> FEATURE:
<223> OTHER INFORMATION: PCR reverse primer

<400> SEQUENCE: 9

| | |
|---|---|
| tggcatccag aagagagaaa | 20 |

<210> SEQ ID NO 10
<211> LENGTH: 17
<212> TYPE: DNA
<213> ORGANISM: artificial sequence
<220> FEATURE:
<223> OTHER INFORMATION: PCR forward primer

<400> SEQUENCE: 10

| | |
|---|---|
| gcatgggtca gaaggat | 17 |

```
<210> SEQ ID NO 11
<211> LENGTH: 17
<212> TYPE: DNA
<213> ORGANISM: artificial sequence
<220> FEATURE:
<223> OTHER INFORMATION: PCR reverse primer

<400> SEQUENCE: 11
ccaatggtga tgacctg                                                   17

<210> SEQ ID NO 12
<211> LENGTH: 33
<212> TYPE: DNA
<213> ORGANISM: artificial sequence
<220> FEATURE:
<223> OTHER INFORMATION: PCR primer

<400> SEQUENCE: 12
ggactcgaga tgactagaat cgacacgtgt gcg                                 33

<210> SEQ ID NO 13
<211> LENGTH: 40
<212> TYPE: DNA
<213> ORGANISM: artificial sequence
<220> FEATURE:
<223> OTHER INFORMATION: PCR primer

<400> SEQUENCE: 13
tgaaagcttc cttaagctgc atggcatcca gaagagagaa                          40

<210> SEQ ID NO 14
<211> LENGTH: 16
<212> TYPE: DNA
<213> ORGANISM: artificial sequence
<220> FEATURE:
<223> OTHER INFORMATION: 5' primer for QPCR

<400> SEQUENCE: 14
agggagcact gtaatc                                                    16

<210> SEQ ID NO 15
<211> LENGTH: 25
<212> TYPE: DNA
<213> ORGANISM: artificial sequence
<220> FEATURE:
<223> OTHER INFORMATION: 3' primer for QPCR

<400> SEQUENCE: 15
tgcatgtgga tcaatttctt ttaga                                          25

<210> SEQ ID NO 16
<211> LENGTH: 27
<212> TYPE: DNA
<213> ORGANISM: artificial sequence
<220> FEATURE:
<223> OTHER INFORMATION: FAM labeled reporter primer

<400> SEQUENCE: 16
ccaacctgag accagattat acatttt                                        27

<210> SEQ ID NO 17
<211> LENGTH: 874
<212> TYPE: DNA
<213> ORGANISM: artificial sequence
<220> FEATURE:
<223> OTHER INFORMATION: pYES/NT vector
```

-continued

```
<400> SEQUENCE: 17
gggttctcat catcatcatc atcatggtat ggctagcatg actggtggac        50
agcaaatggg tcgggatctg tacgacgatg acgataaggt acctaaggat       100
ccagtgtggt ggaattcgcc cttgatgact agaatcgaca cgtgtgcgtg       150
cgcacgcgtg tgcgtgtgtg tgttcatctg tctgcatgtg gatcaatttc       200
ttttagaaaa taatttattg tatgatttat tttggagtta tattctgatt       250
acagtgctcc ctctcccaaa tagcattgat ttttteccec ctctaaaatg       300 tataatctgg tctcaggttg gattctttgg tacatttctc tcttctggat       350
gccatgcagc ttaagaaggg cgaattctgc agatatccag cacagtggcg       400
gccgctcgag tctagagggc ccttcgaagg taagcctatc cctaaccctc       450
tcctcggtct cgattctacg cgtaccggtc atcatcacca tcaccattga       500
gtttaaaccc gctgatccta gagggccgca tcatgtaatt agttatgtca       550
cgcttacatt cacgccctcc ccccacatcc gctctaaccg aaaaggaagg       600
agttagacaa cctgaagtct aggtccctat ttattttttt atagttatgt       650
tagtattaag aacgttattt atatttcaaa tttttctttt ttttctgtac       700
agacgcgtgt acgcatgtaa cattatactg aaaaccttgc ttgagaaggt       750
tttgggacgc tcgaaggctt taatttgcaa gctgcggccc tgcattaatg       800
aatcggccaa cgcgcgggga gaggcggttt gcgtattggg cgctcttccg       850
cttcctcgct cactgactcg ctgc                                   874
```